US012168681B2

(12) United States Patent
Wu et al.

(10) Patent No.: US 12,168,681 B2
(45) Date of Patent: Dec. 17, 2024

(54) IL-2 VARIANTS WITH REDUCED BINDING TO IL-2 RECEPTOR ALPHA AND USES THEREOF

(71) Applicant: Regeneron Pharmaceuticals, Inc., Tarrytown, NY (US)

(72) Inventors: Jiaxi Wu, Pleasantville, NY (US); Tong Zhang, New Rochelle, NY (US); Samuel Davis, New York, NY (US); Nicolin Bloch, Ossining, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/494,355

(22) Filed: Oct. 25, 2023

(65) Prior Publication Data

US 2024/0067690 A1 Feb. 29, 2024

Related U.S. Application Data

(62) Division of application No. 17/234,896, filed on Apr. 20, 2021, now Pat. No. 11,834,485.

(60) Provisional application No. 63/167,188, filed on Mar. 29, 2021, provisional application No. 63/013,058, filed on Apr. 21, 2020.

(51) Int. Cl.

| | |
|---|---|
| ***C07K 14/55*** | (2006.01) |
| ***A61K 38/00*** | (2006.01) |
| ***A61K 38/20*** | (2006.01) |
| ***A61K 45/06*** | (2006.01) |
| ***C07K 14/47*** | (2006.01) |
| ***C07K 14/735*** | (2006.01) |
| ***C07K 14/74*** | (2006.01) |

(52) U.S. Cl.

CPC .......... *C07K 14/55* (2013.01); *A61K 38/2013* (2013.01); *A61K 45/06* (2013.01); *C07K 14/4748* (2013.01); *C07K 14/70535* (2013.01); *C07K 14/70539* (2013.01); *A61K 38/00* (2013.01); *C07K 2319/21* (2013.01); *C07K 2319/30* (2013.01); *C07K 2319/33* (2013.01); *C07K 2319/41* (2013.01)

(58) Field of Classification Search

CPC ................ C07K 14/55; C07K 14/4748; C07K 14/70535; C07K 14/70539; C07K 2319/21; C07K 2319/30; C07K 2319/33; C07K 2319/41; A61K 38/2013; A61K 45/06; A61K 38/00

See application file for complete search history.

(56) References Cited

U.S. PATENT DOCUMENTS

| | | | |
|---|---|---|---|
| 3,773,919 | A | 11/1973 | Boswell et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,596,556 | A | 6/1986 | Morrow et al. |
| 4,790,824 | A | 12/1988 | Morrow et al. |
| 4,941,880 | A | 7/1990 | Burns |
| 5,064,413 | A | 11/1991 | McKinnon et al. |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,811,097 | A | 9/1998 | Allison et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 2020/0247894 | A1 | 8/2020 | Orengo et al. |
| 2022/0363731 | A1 | 11/2022 | Zhao et al. |

FOREIGN PATENT DOCUMENTS

| | | | |
|---|---|---|---|
| WO | 2012107417 | A1 | 8/2012 |
| WO | 2016164937 | A2 | 10/2016 |
| WO | 2020020783 | A1 | 1/2020 |
| WO | 2021030374 | A1 | 2/2021 |

OTHER PUBLICATIONS

Altschul et al., "Gapped BLAST and PSI-BLAST: a new generation of protein database search programs," Nucleic Acids Res. (1997), 25(17):3389-3402.
Altschul et al., "Basic Local Alignment Seach Tool," J. Mol. Biol. (1990), 215:403-10.
Bazan, "Unraveling the Structure of IL-2," Science (1992), 257(5068):410-413.
Bennetzen et al., "The primary structure of the *Saccharomyces cerevisiae* gene for alcohol dehydrogenase," J Biol Chem. (1982); 257(6):3026-31.
Campbell, "Codon Usage in Higher Plants, Green Algae, and Cyanobacteria," Plant Physiol. (Jan. 1990); 92(1):1-11.
Cheng et al., "T-cell tolerance and the multi-functional role of IL-2R signaling in T-regulatory cells, " Immunol Rev (2011), 241(1):63-76.
Hutloff et al., "ICOS is an inducible T-cell co-stimulator structurally and functionally related to CD28," Nature (1999), 397: 263-266 (Abstract).
Imai et al., "Depletion of CD4+CD25+ regulatory T cells enhances interleukin-2-induced antitumor immunity in a mouse model of colon adenocarcinoma," Cancer Sci (2007), 98(3):416-23.

(Continued)

*Primary Examiner* — Jeffrey Stucker
*Assistant Examiner* — Brittney E Donoghue
(74) *Attorney, Agent, or Firm* — Fox Rothschild LLP; Aparna G. Patankar

(57) ABSTRACT

This disclosure relates to IL-2 variants and methods of use thereof, including methods of treating or inhibiting a cancer or tumor. The IL-2 variants may have reduced ability in binding to or activating IL-2Rα. The IL-2 variants may retain the ability in binding to or activating IL-2Rβ and/or IL-2Rγ. In addition, the IL-2 variants may have decreased Treg activity but maintain the capacity to activate NK cells and T effector cells.

5 Claims, 10 Drawing Sheets

Specification includes a Sequence Listing.

(56) References Cited

OTHER PUBLICATIONS

International Search Report and Written Opinion issued Aug. 9, 2021 in International Application No. PCT/US2021/028066 (14 pages).
Kimple et al., "Overview of affinity tags for protein purification," Curr Protoc Protein Sci. (2013), 73:9.9.1-9.9.23.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," OncoImmunology (2017), 6(3):e1277306.
Lenardo, "Interleukin-2 programs mouse alpha beta T lymphocytes for apoptosis," Nature (1991), 353(6347):858-61 (Abstract).
Liao et al., "Cytokine receptor modulation by interleukin-2 broadly regulates T helper cell lineage differentiation," Nat Immunol (2011), 12(6):551-59.
Liao et al., "Priming for T helper type 2 differentiation by interleukin 2-mediated induction of interleukin 4 receptor alpha-chain expression," Nat Immunol (2008), 9(11):1288-96.
Melero et al., "Monoclonal antibodies against the 4-1BB T-cell activation molecule eradicate established tumors," Nature Medicine (1997), 3:682-685.
Meyers et al., "Optimal alignments in linear space," Comput. Appl. Biosci. (1988), 4(1):11-17.
Minami et al., "The IL-2 receptor complex: its structure, function, and target genes," Annu Rev Immunol (1993), 11:245-268 (Abstract).
Mokyr et al., "Realization of the Therapeutic Potential of CTLA-4 Blockade in Low-Dose Chemotherapy-treated Tumor-bearing Mice," Cancer Research (1998), 58: 5301-5304.
Mortara et al., "Anti-Cancer Therapies Employing IL-2 Cytokine Tumor Targeting: Contribution of Innate, Adaptive, and mmunosuppressive Cells in the Anti-tumor Efficacy" Frontiers in Immunology (2018), 9: 1-11, Article 2905.
Morton, "Selection on the codon bias of chloroplast and cyanelle genes in different plant and algal lineages," J Mol Evol. (1998), 46(4):449-59 (Abstract).
Murray et al., "Codon usage in plant genes," Nucleic Acids Res. (1989), 17(2):477-98.
Nakamura et al., "Codon usage tabulated from the international DNA sequence databases: status for the year 2000," Nucl. Acids Res. (2000), 28(1):292.
Needleman et al., "A general method applicable to the search for similarities in the amino acid sequence of two proteins," J. Mol. Biol. (1970), 48(3):444-453 (Abstract).
Nicolaou et al., "A Rationally Designed Molecule with Extremely Potent and Selective DNA Cleaving Properties and Apoptosis Inducing Activity", Agnew Chem Intl Ed Engl. (1994), 33:183-186 (Abstract).
Novellino et al., "A listing of human tumor antigens recognized by T cells: Mar. 2004 update," Cancer Immunol Immunother (2005), 54(3):187-207 (Abstract).
Parmiani et al., "Unique Human Tumor Antigens: Immunobiology and Use in Clinical Trials," J Immunol (2007), 178 (4):1975-79.
Pearson, "Using the FASTA program to search protein and DNA sequence databases.", Methods Mol. Biol. (1994), 24: 307-331.
Ridge et al., "A conditioned dendritic cell can be a temporal bridge between a CD4+ T-helper and a T-killer cell," Nature (1998), 393(6684):474-478.
Sakaguchi, "Naturally arising CD4+ regulatory t cells for immunologic self-tolerance and negative control of immune responses," Annu Rev Immunol (2004), 22:531-62 (Abstract).
Sensi et al., "Unique tumor antigens: evidence for immune control of genome integrity and immunogenic targets for T cell-mediated patient-specific immunotherapy," Clin Cancer Res (2006), 12(17):5023-32.
Smith, "Interleukin-2: inception, impact, and implications," Science (1988), 240(4856):1169-76 (Abstract).
Waldmann, "Albumin Catabolism", Albumin: Structure, Function and Uses (1977), pp. 255-273 (Abstract).
Weinberg et al., "Engagement of the OX-40 Receptor In Vivo Enhances Antitumor Immunity", J Immunol (2000), 164(4):2160-2169.
Yeh et al., "Design of yeast-secreted albumin derivatives for human therapy: biological and antiviral properties of a serum albumin-CD4 genetic conjugate", Proc. Natl. Acad. Sci. USA (1992), 89(5):1904-1908.
Zhu et al., "Differentiation of effector CD4 T cell populations", Annu Rev Immunol (2010), 28:445-89.

| Lane | hIL2-mmh |
|---|---|
| 1 | WT |
| 2 | P34C |
| 3 | F42C |
| 4 | E61C |
| 5 | K64C |
| 6 | P65C |
| 7 | E68C |

| | EC50 |
|---|---|
| Monomer | 1.248e-012 |
| Dimer | 2.872e-010 |

| | EC50 |
|---|---|
| Monomer | 8.348e-010 |
| Dimer | 8.970e-010 |

| | EC50 |
|---|---|
| Monomer | 3.069e-010 |
| Dimer | 2.885e-010 |

IL-2 VARIANTS WITH REDUCED BINDING TO IL-2 RECEPTOR ALPHA AND USES THEREOF

CROSS-REFERENCE TO RELATED APPLICATIONS

This application is a divisional of U.S. patent application Ser. No. 17/234,896 filed Apr. 20, 2021, which claims the benefit of priority to U.S. Provisional Patent Application No. 63/013,058 filed Apr. 21, 2020 and U.S. Provisional Patent Application No. 63/167,188 filed Mar. 29, 2021, the disclosures of all of which are hereby incorporated by reference in their entireties.

SEQUENCE LISTING

The sequence listing of the present application is submitted electronically as an ST.26 formatted xml file with a file name "10729_seqlist_ST26," creation date of Oct. 4, 2023, and a size of 17,880 bytes. This sequence listing submitted is part of the specification and is hereby incorporated by reference in its entirety.

FIELD

The present disclosure relates generally to interleukin-2 (IL-2) variants and more specifically to the IL-2 variants that exhibit reduced ability to bind to or activate IL-2 receptor alpha (IL-2Rα) and methods of using such IL-2 variants.

BACKGROUND

IL-2, also known as T cell growth factor (TCGF), is a 15.5 kDa globular glycoprotein and pluripotent cytokine that plays a central role in lymphocyte generation, survival, and homeostasis. It has a length of 133 amino acids and consists of four antiparallel, amphiphatic α-helices that form a quaternary structure (Smith, *Science,* 240:1169-76 (1988); *Bazan, Science,* 257:410-413 (1992)). IL-2 is produced primarily by activated CD4+ helper T cells, and plays a significant role in producing a normal immune response. IL-2 promotes proliferation and expansion of activated T lymphocytes, potentiates B cell growth, and activates monocytes and natural killer (NK) cells. IL-2 also promotes T helper differentiation and the development of regulatory T (Treg) cells (Zhu et al., *Annual Review of Immunology,* 28:445-89 (2010); Liao et al., *Nat Immunol,* 9:1288-96 (2008); Liao et al., *Nat Immunol* 12:551-59 (2011); Cheng et al., *Immunol Rev,* 241:63-76 (2011)).

IL-2 mediates its action by binding to the IL-2 receptor (IL-2R), which includes up to three individual subunits: alpha (CD25), beta (CD122), and gamma (CD132). These three subunits result in a trimeric, high-affinity receptor for IL-2. Dimeric IL-2 receptor consisting of the beta and gamma subunits is termed intermediate-affinity IL-2R. The alpha subunit forms the monomeric low-affinity IL-2 receptor. Although the dimeric intermediate-affinity IL-2 receptor binds IL-2 with approximately 100-fold lower affinity than the trimeric high-affinity receptor, both the dimeric and the trimeric IL-2 receptor variants are able to transmit signal upon IL-2 binding (Minami et al., *Annu Rev Immunol,* 11:245-268 (1993)).

IL-2 exhibits antitumor effects by its ability to expand lymphocyte populations in vivo and to increase the effector functions of these cells, which makes IL-2 immunotherapy a potential treatment option for certain metastatic cancers.

For example, high-dose IL-2 treatment (Proleukin® (Aldesleukin)) has been approved for use in patients with metastatic renal cell carcinoma and metastatic melanoma.

However, IL-2 has a dual function in the immune response in that it not only mediates expansion and activity of effector cells, but is also involved in maintaining peripheral immune tolerance. For instance, IL-2 is involved in the maintenance of peripheral CD4+CD25+$T_{reg}$ cells, which suppress effector T cells by inhibiting T cell help and activation, or through release of immunosuppressive cytokines such as IL-10 or TGF-beta. Depletion of $T_{reg}$ cells has been shown to enhance IL-2 induced anti-tumor immunity (Imai et al., *Cancer Sci,* 98:416-23 (2007)).

Additionally, IL-2 induces activation-induced cell death (AICD) in T cells. AICD is a process by which fully activated T cells undergo programmed cell death through engagement of cell surface-expressed death receptors such as CD95 (also known as Fas) or the TNF receptor. When antigen-activated T cells expressing a high-affinity IL-2 receptor (after previous exposure to IL-2) during proliferation are re-stimulated with antigen via the T cell receptor (TCR)/CD3 complex, the expression of Fas ligand (FasL) and/or tumor necrosis factor (TNF) is induced, making the cells susceptible to Fas-mediated apoptosis. This process is IL-2 dependent (Lenardo, *Nature,* 353:858-61 (1991)) and mediated via STAT5. The process of AICD in cytolytic T-lymphocytes (CTLs) can establish tolerance not only to self-antigens, but tumor antigens as well. In this sense, IL-2 may not be optimal for inhibiting tumor growth because, in the presence of IL-2, generated CTLs might recognize the tumor as self and undergo AICD, or the immune response might be inhibited by IL-2 dependent $T_{reg}$ cells.

Another challenge of IL-2 immunotherapy arises from adverse side effects whereby patients receiving high-dose IL-2 treatment frequently experience severe cardiovascular, pulmonary, renal, hepatic, gastrointestinal, neurological, cutaneous, hematological, and systemic adverse events that require intensive monitoring and in-patient management. The majority of these side effects can be explained by the development of so-called vascular (or capillary) leak syndrome (VLS), a pathological increase in vascular permeability leading to fluid extravasation in multiple organs causing, e.g., pulmonary and cutaneous edema and liver cell damage, and intravascular fluid depletion causing a drop in blood pressure and compensatory increase in heart rate. Low-dose IL-2 regimens have been tested in patients to avoid VLS, but with suboptimal therapeutic results.

Thus, there is a need for novel IL-2 variants that provide improved immunotherapy with reduced toxicity for treating or inhibiting tumor.

SUMMARY

This disclosure addresses the need mentioned above in a number of aspects. In one aspect, this disclosure provides an isolated IL-2 variant comprising one or more modifications, wherein the IL-2 variant exists at least partially in a dimeric form, and wherein the IL-2 variant has reduced ability to bind to and/or activate IL-2 receptor a (IL-2Rα) as compared to an IL-2 polypeptide of SEQ ID NO: 1 or 2, while retaining the ability to bind to and/or activate IL-2Rβ and IL-2Rγ.

In some embodiments, the isolated IL-2 variant exhibits about 30 fold decrease in potency in activating IL-2Rα as compared to the IL-2 polypeptide of SEQ ID NO: 2 or SEQ ID NO: 11. In some embodiments, the isolated IL-2 variant exhibits about 10 fold decrease in potency in activating IL-2Rα as compared to the IL-2 polypeptide of SEQ ID NO: 12.

In some embodiments, the modifications may include a cysteine substitution. In some embodiments, the isolated IL-2 variant comprises a disulfide bond that stabilizes the isolated IL-2 variant in the dimeric form. In some embodiments, the cysteine substitution is selected from the group consisting of P34C, F42C, E61C, K64C, P65C, and E68C substitutions. In some embodiments, the cysteine substitution is an E68C substitution.

In some embodiments, the isolated IL-2 variant comprises a polypeptide sequence having at least 80% (e.g., 80%, 85%, 90%, 95%, 99%) identity to SEQ ID NOs: 3-9 while the cysteine substitution is maintained. In some embodiments, the isolated IL-2 variant comprises a polypeptide sequence of SEQ ID NOs: 3-9. In some embodiments, the isolated IL-2 variant comprises a polypeptide sequence of SEQ ID NO: 3 or 4.

In some embodiments, the isolated IL-2 variant further comprises an Fc domain dimer, wherein each Fc domain monomer is operably linked to an IL-2 variant polypeptide. In some embodiments, the Fc domain monomer is operably linked to the IL-2 variant polypeptide via a peptide linker or a non-peptide linker. In some embodiments, the isolated IL-2 variant comprises a polypeptide sequence having at least 80% (e.g., 80%, 85%, 90%, 95%, 99%) identity to SEQ ID NOs: 11-12 or a polypeptide sequence of SEQ ID NO: 11 or 12.

In some embodiments, the dimeric form of the IL-2 variant is stabilized by a crosslinker.

In some embodiments, the isolated IL-2 variant is linked to a detectable tag or a detectable marker. In some embodiments, the detectable tag is a myc-myc-hexahistidine (mmh) tag. In some embodiments, the detectable tag is linked to the N- and/or C-terminus of the isolated IL-2 variant.

In some embodiments, the isolated IL-2 variant is linked to IL-2 receptor alpha, optionally by a disulfide bond. In some embodiments, the isolated IL-2 variant is linked to a targeting moiety that binds to a tumor-associated antigen, an antigen in the extracellular matrix in a tumor, an immunotherapeutic agent, an immune checkpoint modulator, or a peptide-MHC complex.

In another aspect, this disclosure also provides a pharmaceutical composition comprising the isolated IL-2 variant described above and optionally a pharmaceutically acceptable carrier or excipient. In some embodiments, the pharmaceutical composition further comprises a second therapeutic agent. In some embodiments, the second therapeutic agent is an anti-cancer or anti-tumor agent.

Also provided in this disclosure are: (a) an isolated polynucleotide molecule comprising a polynucleotide sequence that encodes the isolated IL-2 variant described above. In some embodiments, the polynucleotide sequence may include a polynucleotide sequence of SEQ ID NO: 10; (b) a vector comprising the polynucleotide sequence, as described above; (c) a host cell comprising the described vector; and (d) a method for producing a polypeptide, comprising culturing the host cell, as described above, under conditions in which the polynucleotide molecule is expressed. This disclosure further provides a kit comprising a pharmaceutically acceptable dose unit of a pharmaceutically effective amount of the above-described isolated IL-2 variant.

In another aspect, this disclosure provides a method of reducing $T_{reg}$ cell activity. The method comprises administering a therapeutically effective amount of the isolated IL-2 variant or the pharmaceutical composition, as described above, to a subject in need thereof. In some embodiments, the subject may have or be suspected of a cancer or tumor. In some embodiments, the subject exhibits reduced adverse events as compared to a subject treated with human wild-type IL-2.

In yet another aspect, this disclosure additionally provides a method of treating or inhibiting a tumor. The method comprises administering a therapeutically effective amount of the isolated IL-2 variant or the pharmaceutical composition, as described above, to a subject in need thereof.

In some embodiments, the isolated IL-2 variant is administered in combination with a second therapeutic agent or therapy. In some embodiments, the second therapeutic agent is an anti-cancer or anti-tumor agent.

In some embodiments, the isolated IL-2 variant is administered intratumorally, intravenously, subcutaneously, intraosseously, orally, transdermally, or sublingually.

In some embodiments, the cancer or tumor is selected from the group consisting of oral cancer, oropharyngeal cancer, nasopharyngeal cancer, respiratory cancer, urogenital cancer, gastrointestinal cancer, central or peripheral nervous system tissue cancer, endocrine or neuroendocrine cancer or hematopoietic cancer, glioma, sarcoma, carcinoma, lymphoma, melanoma, fibroma, meningioma, brain cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer, and skin cancer.

Also provided is use of the isolated IL-2 variant, as described above, for reducing $T_{reg}$ cell activity in a subject.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 2A shows mass spectra of indicated peptides from D2O-treated IL-2(WT) or IL-2 (E68C) protein samples. Dashed lines indicate the centroid masses of each peptide in the indicated samples. Arrows indicate shifts in the centroid mass of the same peptide from different samples. Differences in the percentage of deuterium uptake (% D) for each peptide were shown. Compared to corresponding peptides from IL-2(WT) monomer, two peptides from hIL-2(E68C) dimer were significantly protected from deuterium uptake. These two peptides correspond to residues 42-52 (FKFYMPKKATE) and 69-84 (VLNLAQSKNFHLRPRD) and appear to surround the mutated E68C residue. FIG. 2B shows a surface structure model of human IL-2 (PDB: 1M47) with the positions of protected residues and mutated E68C residue indicated.

FIG. 3A shows a structural representation of IL-2 receptors (IL-2α, IL-2β, and IL-2γ) in complex with IL-2 (WT) (PDB: 2B5I). FIG. 3B shows a structural representation of IL-2 receptors (IL-2α, IL-2β, and IL-2γ) in complex with modeled IL-2 (E68C) dimer based on the dimeric interface shown in FIG. 2B.

FIG. 4A shows a purification scheme of IL-2(E68C)-mmh protein. Aliquots of each fraction from the Superdex 75 column were analyzed by SDS-PAGE followed by staining with Coomassie blue (FIG. 4B) and tested for their activity on NK92-STAT3-Luc cells (FIG. 4C).

DETAILED DESCRIPTION

Figure 1:
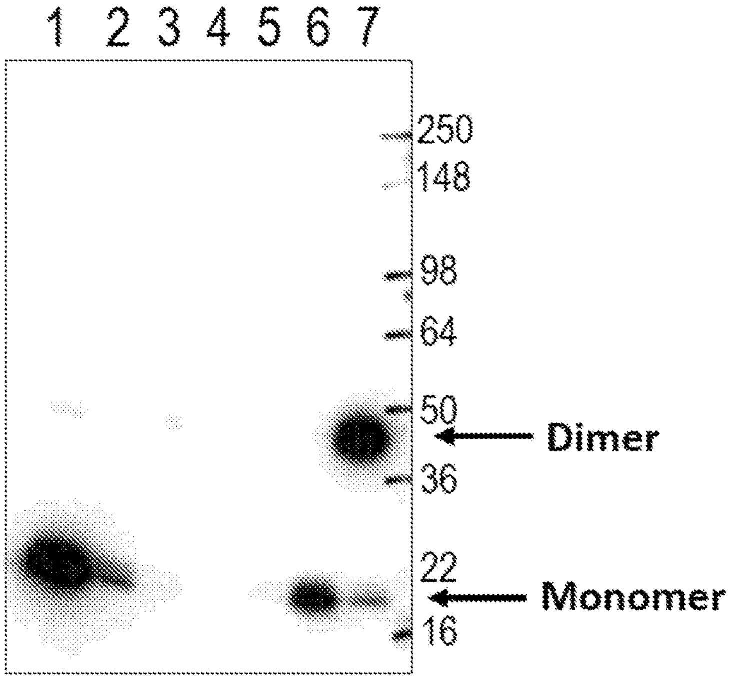
FIG. 1 shows Western blot results under a non-reducing condition for the IL-2 variants having a cysteine substitution at the binding interface between IL-2 and IL-2Rα. Of these IL-2 variants, human IL-2 (E68C) (or hIL-2 (E68C)) forms a stable disulfide-bonded dimer. Plasmids encoding indicated hIL-2 variants tagged with a myc-myc-hexahistidine (mmh) tag to their C-termini were transfected into Expi293F™ cells. Supernatants were immunoblotted with an anti-Myc antibody after SDS-PAGE under a non-reducing condition.

This disclosure provides novel IL-2 variants with reduced ability in binding to and/or activating IL-2Rα. In some embodiments, the IL-2 variants disclosed herein retain the ability in binding to and/or activating IL-2Rβ and/or IL-2Rβγ. In some embodiments, the IL-2 variants have decreased Treg activity but maintain the capacity to activate NK cells and T effector cells. In some embodiments, the IL-2 variants exhibit anti-tumor efficacy with reduced toxicity.

A. IL-2 VARIANTS AND COMPOSITIONS a. IL-2 Variants

In one aspect, this disclosure provides an IL-2 variant comprising one or more modifications (e.g., genetic modifications). In some embodiments, the IL-2 variant has reduced ability to bind to and/or activate IL-2Rα as compared to a wild-type IL-2 protein, for example, the human wild-type IL-2 protein as represented by SEQ ID NO: 1 or 2.

In some embodiments, the isolated IL-2 variant exhibits at least about 10 fold (e.g., 10 fold, 15 fold, 20 fold, 25 fold, 30 fold, 35 fold, 40 fold) decrease in potency in activating IL-2Rα as compared to the IL-2 polypeptide of SEQ ID NO: 2 (REGN7183) or SEQ ID NO: 11 (REGN8189). In some embodiments, athe isolated IL-2 variant exhibits at least about 3 fold (e.g., 3 fold, 5 fold, 8 fold, 10 fold, 15 fold, 20 fold) decrease in potency in activating IL-2Rα as compared to the IL-2 polypeptide of SEQ ID NO: 12 (REGN8190).

In some embodiments, the IL-2 variant retains the ability to bind to and/or activate IL-2Rβ and/or IL-2Rγ. As a result, the IL-2 variant may compete with the wild-type IL-2 protein for binding of IL-2 receptor, for example, by competing with the wild-type IL-2 protein for the binding sites on IL-2Rβ and/or IL-2Rγ.

The term “isolated” when referring to polypeptides means that the polypeptide is substantially free from at least one other component with which it is associated or found together in nature.

The term “interleukin-2” or “IL-2” as used herein, refers to any native IL-2 from any vertebrate source, including mammals such as primates (e.g., humans) and rodents (e.g., mice and rats), unless otherwise indicated. The term encompasses unprocessed IL-2 as well as any form of IL-2 that results from processing in the cell. The term also encompasses naturally occurring variants of IL-2, e.g., splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule.

The term “IL-2 variant” or “IL-2 variant polypeptide” as used herein is intended to encompass any forms of modifications of various forms of the IL-2 molecule, including full-length IL-2, truncated forms of IL-2 and forms where IL-2 is linked to another molecule such as by fusion or chemical conjugation. “Full-length,” when used in reference to IL-2, is intended to mean the mature, natural length IL-2 molecule. The various forms of IL-2 mutants are characterized in having at least one amino acid mutation affecting the interaction of IL-2 with IL-2Rα. This mutation may involve substitution, deletion, truncation, or modification of the wild-type amino acid residue normally located at that position. In some embodiments, IL-2 mutants or variants obtained by amino acid substitution. In some embodiments, an IL-2 variant may be referred to herein as an IL-2 mutant peptide sequence, an IL-2 mutant polypeptide, IL-2 mutant protein, or IL-2 mutant analog. Designation of various forms of IL-2 is herein made with respect to the sequence shown in SEQ ID NO: 1. Various designations may be used herein to indicate the same mutation. For example, a mutation from glutamate at position 68 to cysteine can be indicated as 68C, C68, E68C, or Glu68Cys.

Generally, the modifications may include any in vivo or in vitro modifications, such as truncation, fusion, mutation, phosphorylation, glycosylation, ubiquitination, nitrosylation, methylation, acetylation, lipidation, and proteolysis. The term “mutation” or “amino acid mutation” as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to IL-2Rα. Amino acid sequence deletions and insertions include amino- and/or carboxy-terminal deletions and insertions of amino acids. An example of a terminal deletion is the deletion of the alanine residue in position 1 of full-length human IL-2. For the purpose of altering, e.g., the binding characteristics of an IL-2 polypeptide, non-conservative amino acid substitutions, i.e., replacing one amino acid with another amino acid having different structural and/or chemical properties, may be performed. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis, and the like. It is contemplated that methods of altering the side chain group of an amino acid by methods other than genetic engineering, e.g., chemical modification, may also be useful.

In some embodiments, the one or more modifications of the IL-2 variant may be located at the binding interface to IL-2Rα. In some embodiments, such modifications may reduce the binding affinity of the IL-2 variant to IL-2Rα. In some embodiments, such modifications may disrupt the binding of the IL-2 variant to IL-2Rα. In some embodiments, the one or more modifications of the IL-2 variant may include a mutation at the P34, F42, E61, K64, or E68 position. In some embodiments, the one or more modifications of the IL-2 variant may include a cysteine substitution, such as P34C, F42C, E61C, K64C, P65C, or E68C substitution. In some embodiments, the cysteine substitution is an E68C substitution.

In some embodiments, the IL-2 variant exhibits reduced binding affinity to IL-2Rα. “Affinity” refers to the strength of the total of non-covalent interactions between a single binding site of a molecule (e.g., a receptor), such as IL-2Rα, and its binding partner (e.g., a ligand), such as IL-2. Unless indicated otherwise, as used herein, “binding affinity” refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, such as isothermal titration calorimetry (ITC), surface plasmon resonance (SPR), MicroScale Thermophoresis (MST), and Bio-Layer Interferometry (BLI).

For example, the affinity of the mutant or wild-type IL-2 polypeptide to various forms of the IL-2 receptor can be determined by SPR, using standard instrumentation such as a BPAcore instrument (GE HEALTHCARE) and receptor subunits. Alternatively, binding affinity of IL-2 variants to different forms of the IL-2 receptor may be evaluated using cell lines known to express one or the other form of the receptor.

TABLE 1

Example Sequences of IL-2 Wild-Type and Variants

| SEQ ID NO | Sequence | Description |
|---|---|---|
| 1 | MYRMQLLSCIALSLALVTNSAPTSSSTKKTQLQ<br>LEHLLLDLQMILNGINNYKNPKLTRMLTFKFYM<br>PKKATELKHLQCLEEELKPLEEVLNLAQSKNFH<br>LRPRDLISNINVIVLELKGSETTFMCEYADETATI<br>VEFLNRWITFCQSIISTLT | Human IL-2 WT sequence (UniProt: P60568) with signal peptide (underlined) |
| 2 | APTSSSTKKTQLQLEHLLLDLQMILNGINNYKNP<br>KLTRMLTFKFYMPKKATELKHLQCLEEELKPLE<br>EVLNLAQSKNFHLRPRDLISNINVIVLELKGSETT<br>FMCEYADETATIVEFLNRWITFCQSIISTLTEQKL<br>ISEEDLGGEQKLIS EEDLHHHHHH | hIL2-mmh (REGN7183): Monomeric human IL-2 with a C-terminal myc-myc-hexahistidine (mmh) tag (underlined) |
| 3 | APTSSSTKKTQLQLEHLLLDLQMILNGINNYKNP<br>KLTRMLTFKFYMPKKATELKHLQCLEEELKPLE<br>CVLNLAQSKNFHLRPRDLISNINVIVLELKGSET<br>TFMCEYADETATIVEFLNRWITFCQSIISTLTEQ<br>KLISEEDLGGEQKLIS EEDLHHHHHH | hIL2(E68C)-mmh (REGN7184): Dimeric human IL-2 (E68C) with a C-terminal myc-myc-hexahistidine (mmh) tag (underlined) |
| 4 | APTSSSTKKTQLQLEHLLLDLQMILNGINNYKNP<br>KLTRMLTFKFYMPKKATELKHLQCLEEELKPLE<br>CVLNLAQSKNFHLRPRDLISNINVIVLELKGSET<br>TFMCEYADETATIVEFLNRWITFCQSIISTLT | hIL-2(E68C) |
| 5 | APTSSSTKKTQLQLEHLLLDLQMILNGINNYKN<br>CKLTRMLTFKFYMPKKATELKHLQCLEEELKPL<br>EEVLNLAQSKNFHLRPRDLISNINVIVLELKGSET<br>TFMCEYADETATIVEFLNRWITFCQSIISTLT | hIL-2(P34C) |

TABLE 1-continued

Example Sequences of IL-2 Wild-Type and Variants

| SEQ ID NO | Sequence | Description |
|---|---|---|
| 6 | APTSSSTKKTQLQLEHLLLDLQMILNGINNYKNP<br>KLTRMLTCKFYMPKKATELKHLQCLEEELKPLE<br>EVLNLAQSKNFHLRPRDLISNINVIVLELKGSETT<br>FMCEYADETATIVEFLNRWITFCQSIISTLT | hIL-2(F42C) |
| 7 | APTSSSTKKTQLQLEHLLLDLQMILNGINNYKNP<br>KLTRMLTFKFYMPKKATELKHLQCLECELKPLE<br>EVLNLAQSKNFHLRPRDLISNINVIVLELKGSETT<br>FMCEYADETATIVEFLNRWITFCQSIISTLT | hIL-2(E61C) |
| 8 | APTSSSTKKTQLQLEHLLLDLQMILNGINNYKNP<br>KLTRMLTFKFYMPKKATELKHLQCLEEELCPLE<br>EVLNLAQSKNFHLRPRDLISNINVIVLELKGSETT<br>FMCEYADETATIVEFLNRWITFCQSIISTLT | hIL-2(K64C) |
| 9 | APTSSSTKKTQLQLEHLLLDLQMILNGINNYKNP<br>KLTRMLTFKFYMPKKATELKHLQCLEEELKCLE<br>EVLNLAQSKNFHLRPRDLISNINVIVLELKGSETT<br>FMCEYADETATIVEFLNRWITFCQSIISTLT | hIL-2(P65C) |
| 10 | GCACCTACTTCAAGTTCTACAAAGAAAACACA<br>GCTACAACTGGAGCATTTACTGCTGGATTTAC<br>AGATGATTTTGAATGGAATTAATAATTACAAG<br>AATCCCAAACTCACCAGGATGCTCACATTTAA<br>GTTTTACATGCCCAAGAAGGCCACAGAACTG<br>AAACATCTTCAGTGTCTAGAAGAAGAACTCA<br>AACCTCTGGAGTGTGTGCTAAATTTAGCTCAA<br>AGCAAAAACTTTCACTTAAGACCCAGGGACTT<br>AATCAGCAATATCAACGTAATAGTTCTGGAAC<br>TAAAGGGATCTGAAACAACATTCATGTGTGA<br>ATATGCTGATGAGACAGCAACCATTGTAGAAT<br>TTCTGAACAGATGGATTACCTTTTGTCAAAGC<br>ATCATCTCAACACTGACTTGA | cDNA sequence of hIL-<br>2(E68C) |
| 11 | APTSSSTKKTQLQLEHLLLDLQMILNGINNYKNP<br>KLTRMLTFKFYMPKKATELKHLQCLEEELKPLE<br>EVLNLAQSKNFHLRPRDLISNINVIVLELKGSETT<br>FMCEYADETATIVEFLNRWITFCQSIISTLIGGG<br>GSESKYGPPCPPCPAPPVAGPSVFLFPPKPKDTL<br>MISRTPEVTCVVVDVSQEDPEVQFNWYVDGVE<br>VHNAKTKPREEQFNSTYRVVSVLTVLHQDWLN<br>GKEYKCKVSNKGLPSSIEKTISKAKGQPREPQVY<br>TLPPSQEEMTKNQVSLTCLVKGFYPSDIAVEWE<br>SNGQPENNYKTTPPVLDSDGSFFLYSRLTVDKS<br>RWQEGNVFSCSVMHEALHNHYTQKSLSLSLGK | REGN8189<br>IL-2-Fc |
| 12 | APTSSSTKKTQLQLEHLLLDLQMILNGINNYKNP<br>KLTRMLTAKFAMPKKATELKHLQCLEEELKPLE<br>EVLNGAQSKNFHLRPRDLISNINVIVLELKGSET<br>TFMCEYADETATIVEFLNRWITFCQSIISTLTGGG<br>GSESKYGPPCPPCPAPPVAGPSVFLFPPKPKDTL<br>MISRTPEVTCVVVDVSQEDPEVQFNWYVDGVE<br>VHNAKTKPREEQFNSTYRVVSVLTVLHQDWLN<br>GKEYKCKVSNKGLPSSIEKTISKAKGQPREPQVY<br>TLPPSQEEMTKNQVSLTCLVKGFYPSDIAVEWE<br>SNGQPENNYKTTPPVLDSDGSFFLYSRLTVDKS<br>RWQEGNVFSCSVMHEALHNHYTQKSLSLSLGK | REGN8190<br>IL-2(3m)-Fc |

In some embodiments, the IL-2 variant comprises a polypeptide sequence having at least 75% identity (e.g., 75%, 80%, 85%, 90%, 95%, 99%) to SEQ ID NOs: 3-9 while the cysteine substitution is maintained. In some embodiments, the IL-2 variant comprises a polypeptide sequence of SEQ ID NOs: 3-9. In some embodiments, the IL-2 variant comprises a polypeptide sequence of SEQ ID NO: 3 or 4.

As used herein, the term "variant" refers to a first molecule that is related to a second molecule (also termed a "parent" molecule). The variant molecule can be derived from, isolated from, based on or homologous to the parent molecule. For example, the mutant forms of IL-2, including the IL-2 mutant with a cysteine substitution, are variants of the wild-type IL-2. The term variant can be used to describe either polynucleotides or polypeptides.

As applied to proteins, a variant polypeptide can have an entire amino acid sequence identity with the original parent polypeptide or can have less than 100% amino acid identity with the parent protein. For example, a variant of an amino acid sequence can be a second amino acid sequence that is at least 50%, 60%, 70%, 80%, 90%, 95%, 98%, 99% or more identical in amino acid sequence compared to the original amino acid sequence. Polypeptide variants include polypeptides comprising the entire parent polypeptide, and further comprising additional fused amino acid sequences. Polypeptide variants also include polypeptides that are portions or subsequences of the parent polypeptide, for example, unique subsequences (e.g., as determined by standard sequence comparison and alignment techniques) of the polypeptides disclosed herein are also encompassed by the invention.

In another aspect, polypeptide variants include polypeptides that contain minor, trivial, or inconsequential changes to the parent amino acid sequence. For example, minor, trivial, or inconsequential changes include amino acid changes (including substitutions, deletions, and insertions) that have little or no impact on the biological activity of the polypeptide, and yield functionally identical polypeptides, including additions of non-functional peptide sequence. In other aspects, the variant polypeptides of the invention change the biological activity of the parent molecule. One of skill will appreciate that many variants of the disclosed polypeptides are encompassed by the invention.

In some aspects, polynucleotide or polypeptide variants of the invention can include variant molecules that alter, add or delete a small percentage of the nucleotide or amino acid positions, for example, typically less than about 10%, less than about 5%, less than 4%, less than 2% or less than 1%.

A "functional variant" of a protein as used herein refers to a variant of such protein that retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide, or peptide. Functional variants may be naturally occurring or may be man-made.

In some embodiments, the IL-2 variant may include one or more conservative modifications. The IL-2 variant with one or more conservative modifications may retain the desired functional properties, which can be tested using the functional assays known in the art. As used herein, the term "conservative sequence modifications" refers to amino acid modifications that do not significantly affect or alter the binding characteristics of the protein containing the amino acid sequence. Such conservative modifications include amino acid substitutions, additions, and deletions. Modifications can be introduced by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, tryptophan); nonpolar side chains (e.g., alanine, valine, leucine, isoleucine, proline, phenylalanine, methionine); beta-branched side chains (e.g., threonine, valine, isoleucine); and aromatic side chains (e.g., tyrosine, phenylalanine, tryptophan, histidine). includes one or more conservative modifications. The Cas protein with one or more conservative modifications may retain the desired functional properties, which can be tested using the functional assays known in the art. As used herein, the term "conservative sequence modifications" refers to amino acid modifications that do not significantly affect or alter the binding characteristics of the protein containing the amino acid sequence. Such conservative modifications include amino acid substitutions, additions, and deletions. Modifications can be introduced by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, tryptophan); nonpolar side chains (e.g., alanine, valine, leucine, isoleucine, proline, phenylalanine, methionine); beta-branched side chains (e.g., threonine, valine, isoleucine); and aromatic side chains (e.g., tyrosine, phenylalanine, tryptophan, histidine).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

In some embodiments, the isolated IL-2 variant can be conjugated or linked to a detectable tag or a detectable marker (e.g., a radionuclide, a fluorescent dye, or an MRI-detectable label). In some embodiments, the detectable tag can be an affinity tag. The term "affinity tag" as used herein relates to a moiety attached to a polypeptide, which allows the polypeptide to be purified from a biochemical mixture. Affinity tags can consist of amino acid sequences or can include amino acid sequences to which chemical groups are attached by post-translational modifications. Non-limiting examples of affinity tags include His-tag, CBP-tag (CBP:

calmodulin-binding protein), CYD-tag (CYD: covalent yet dissociable NorpD peptide), Strep-tag, StrepII-tag, FLAG-tag, HPC-tag (HPC: heavy chain of protein C), GST-tag (GST: glutathione S transferase), Avi-tag, biotinylated tag, Myc-tag, a myc-myc-hexahistidine (mmh) tag 3×FLAG tag, a SUMO tag, and MBP-tag (MBP: maltose-binding protein). Further examples of affinity tags can be found in Kimple et al., Curr Protoc Protein Sci. 2013 Sep. 24; 73: Unit 9.9.

In some embodiments, the detectable tag can be conjugated or linked to the N- and/or C-terminus of the IL-2 variant. The detectable tag and the affinity tag may also be separated by one or more amino acids. In some embodiments, the detectable tag can be conjugated or linked to the IL-2 variant via a cleavable element. In the context of the present invention, the term "cleavable element" relates to peptide sequences that are susceptible to cleavage by chemical agents or enzyme means, such as proteases. Proteases may be sequence-specific (e.g., thrombin) or may have limited sequence specificity (e.g., trypsin). Cleavable elements I and II may also be included in the amino acid sequence of a detection tag or polypeptide, particularly where the last amino acid of the detection tag or polypeptide is K or R.

In some embodiments, the isolated IL-2 variant is linked to IL-2 receptor alpha, optionally by a disulfide bond.

In some embodiments, the isolated IL-2 variant can be conjugated or linked to at least one polymer (e.g., polyethylene glycol (PEG)), sugar moiety (e.g., N-acetyl galactosamine (GalNAc), triantennary GalNAc), antibody or a fragment thereof (e.g., Fc domain), drug molecule (e.g., anti-cancer or anti-tumor drugs).

In some embodiments, the isolated IL-2 variant can be fused to albumin (e.g., human serum albumin (HSA)) or fragments or variants of albumin. Human serum albumin possesses many desirable characteristics. HSA is found throughout the body, but more specifically in the interstitial space and in blood at serum concentrations of 40 g/L, which is equivalent to 0.7 mM (Yeh et al., Proc. Natl. Acad. Sci. USA, 89:1904-1908 (1992)). HSA is considered to be the most abundant protein of the serum and is responsible for maintaining osmolarity. HSA has favorable pharmacokinetic properties and is cleared very slowly by the liver displaying in vivo half-lives up to several weeks (Yeh et al., Proc. Natl. Acad. Sci. USA, 89:1904-1908 (1992); Waldmann, T. A., Albumin Structure, Function and Uses, pp. 255-273 (1977)). HSA lacks enzymatic activity and antigenicity thereby eliminating potentially undesirable side effects. In this context, HSA acts as a carrier for endogenous as well as exogenous ligands (e.g., IL-2 variants). Combined, these features can be extended, at least partially, onto albumin fusion proteins.

In some embodiments, the isolated IL-2 variant can be fused to a moiety for targeting tumor cells. Such moiety may bind to a tumor-associated antigen (e.g., PSMA, MUC16); bind to a tumor microenvironment antigen (ECM); binds to a cell surface molecule of tumor-reactive lymphocytes (e.g., anti-PD1, anti-LAG3, etc.); binds to a checkpoint inhibitor; or binds to a peptide-MHC complex. For example, tumor-associated antigens that may be targeted include, but are not limited to, alphafetoprotein (AFP), a-actinin-4, A3, antigen specific for A33 antibody, ART-4, B7, Ba 733, BAGE, BrE3-antigen, CA125, CAMEL, CAP-1, carbonic anhydrase IX, CASP-8/m, CCCL19, CCCL21, CD1, CDla, CD2, CD3, CD4, CD5, CD8, CD11A, CD 14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIFla, colon-specific antigen-p (CSAp), CEA (CEACAM5), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gplOO, GRO-β, HLA-DR, HM1.24, human chorionic gonadotropin (HCG) and its subunits, HER2/neu, HMGB-1, hypoxia inducible factor (HIF-1), HSP70-2M, HST-2, la, IGF-1R, BFN-γ, IFN-a, IFN-β, IFN-λ, IL4R, IL-6R, IL-13R, IL-15R, IL-17R, IL-18R, IL-2, IL-6, IL-8, IL-12, IL-15, DL-17, IL-18, IL23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD-1 receptor, placental growth factor, p53, PLAGL2, prostatic acid phosphatase, PSA, PRAME, PSMA, PIGF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1,17-1 A-antigen, complement factors C3, C3a, C3b, C5a, C5, an angiogenesis marker, bcl-2, bcl-6, Kras, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187207).

In some embodiments, the isolated IL-2 variant is linked to a targeting moiety, wherein the targeting moiety binds to a tumor-associated antigen, an antigen in the extracellular matrix in a tumor, an immunotherapeutic agent, an immune checkpoint modulator, or a peptide-MHC complex.

As used herein, the term "conjugate" or "conjugation" or "linked" as used herein refers to the attachment of two or more entities to form one entity. A conjugate encompasses both peptide-small molecule conjugates as well as peptide-protein/peptide conjugates.

The term "fusion polypeptide" or "fusion protein" means a protein created by joining two or more polypeptide sequences together. The fusion polypeptides encompassed in this invention include translation products of a chimeric gene construct that joins the nucleic acid sequences encoding a first polypeptide with the nucleic acid sequence encoding a second polypeptide to form a single open reading frame. In other words, a "fusion polypeptide" or "fusion protein" is a recombinant protein of two or more proteins which are joined by a peptide bond or via several peptides. The fusion protein may also comprise a peptide linker between the two domains.

The term "linker" refers to any means, entity, or moiety used to join two or more entities. A linker can be a covalent linker or a non-covalent linker. Examples of covalent linkers include covalent bonds or a linker moiety covalently attached to one or more of the proteins or domains to be linked. The linker can also be a non-covalent bond, e.g., an organometallic bond through a metal center such as a platinum atom. For covalent linkages, various functionalities can be used, such as amide groups, including carbonic acid derivatives, ethers, esters, including organic and inorganic esters, amino, urethane, urea and the like. To provide for linking, the domains can be modified by oxidation, hydroxylation, substitution, reduction etc. to provide a site for coupling. Methods for conjugation are well known by persons skilled in the art and are encompassed for use in the present invention. Linker moieties include, but are not limited to, chemical linker moieties, or for example, a peptide linker moiety (a linker sequence).

b. Polynucleotides and Cells

Also provided in this disclosure are (i) an isolated polynucleotide molecule comprising a polynucleotide sequence that encodes the isolated IL-2 variant described above. In some embodiments, the polynucleotide sequence may include a polynucleotide sequence of SEQ ID NO: 10; (ii) a vector comprising the polynucleotide sequence, as described above; (iii) a host cell comprising the described vector; and (iv) a method for producing a polypeptide, comprising culturing the host cell, as described above, under conditions in which the polynucleotide molecule is expressed. This disclosure further provides a kit comprising a pharmaceutically acceptable dose unit of a pharmaceutically effective amount of the above-described isolated IL-2 variant.

A "nucleic acid" or "polynucleotide" refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

In some embodiments, the disclosed IL-2 variant can be encoded by a codon-optimized sequence. For example, the nucleotide sequence encoding the IL-2 variant may be codon-optimized for expression in a eukaryote or eukaryotic cell. In some embodiments, the codon-optimized IL-2 variant is codon-optimized for operability in a eukaryotic cell or organism, e.g., a yeast cell, or a mammalian cell or organism, including a mouse cell, a rat cell, and a human cell or non-human eukaryote organism.

Generally, codon optimization refers to a process of modifying a nucleic acid sequence to enhance expression in the host cells by substituting at least one codon of the native sequence with codons that are more frequently or most frequently used in the genes of that host cell while maintaining the native amino acid sequence. Various species exhibit a particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/, and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.). In some embodiments, one or more codons (e.g., 1, 2, 3, 4, 5, 10, 15, 20, 25, 50, or more, or all codons) in a sequence encoding a DNA/RNA-targeting IL-2 variant corresponds to the most frequently used codon for a particular amino acid. As to codon usage in yeast, reference is made to the online Yeast Genome database available at www.yeastgenome.org/community/codonusage.shtml, or *Codon selection in yeast*, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11; as well as *Codon usage in plant genes*, Murray et al., Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode mutant IL-2 polypeptides or immunoconjugates of the invention or fragments thereof.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progenies that have the same function or biological activity as screened or selected for in the originally transformed cell are included herein.

c. IL-2 Dimeric Forms

In some embodiments, the IL-2 variant exists partially, predominantly, or entirely in a dimeric form.

As used herein, the term "partially" as used herein means that a particular oligomeric species, such as dimeric IL-2 variant, is present with other oligomeric species (e.g., IL-2 monomers). For example, the IL-2 variant may "partially" exist as in a dimer form (e.g., homodimer) when at least 1% (e.g., 5%, 10%, 15%, 20%, 25%, 30%, 35%, 40%, 45%, 49%, 50%, 55%, 60%, 65%, 70%, 75%, 80%, 90%, 95%, 99%) of the IL-2 variant molecules exist as a dimer and the rest of the IL-2 variant molecules exist as a monomer.

The term "predominantly" as used herein means that a particular oligomeric species, such as dimeric IL-2 variant, is present in greater mole percent than any other individual oligomeric species. For example, the IL-2 variant may "predominantly" exist as in a dimer form (e.g., homodimer) when 51% of the IL-2 variant molecules exist as a dimer and 49% of the IL-2 variant molecules exist as a monomer.

In some embodiments, the isolated IL-2 variant comprises at least one intermolecular disulfide bond that stabilizes the IL-2 variant in the dimeric form. In some embodiments, the disulfide bond may be formed between two cysteine residues respectively located in the two IL-2 variant monomers. Such cysteine residues may be provided through genetic modifications, such an E68C substitution.

In some embodiments, such cysteine substitution can be identified through cysteine-scanning mutagenesis. Cysteine-scanning mutagenesis entails adding or substituting cysteine residues for individual amino acids in the polypeptide chain and determining the effect of the cysteine substitution on biological activity. Cysteine scanning mutagenesis is similar to alanine-scanning mutagenesis (Cunningham et al., 1992), except that target amino acids are individually replaced with cysteine rather than alanine residues. In some embodiments, amino acids replaced with cysteine thereby promoting formation of a dimeric form of the IL-2 variant are preferred sites for creating cysteine-added IL-2 variants. Such amino acids can be identified by performing cysteine-scanning mutagenesis on the IL-2 and measuring effects on dimer formation.

Suitable methods for determining oligomeric states of a protein are well-known in the art. For example, biophysical analysis for studying the aggregation properties of proteins may include without limitations analytical ultracentrifugation (AUC) (e.g., sedimentation velocity AUC (SV-AUC)), size exclusion chromatography (SEC), SEC-MALS (SEC with combined with multi-angle light scattering), dynamic light scattering (DLS), sodium dodecyl sulfate-polyacrylamide gel electrophoresis (SDS-Page), native SDS-PAGE, field flow fractionation (FFF), electron microscopy (EM), cryogenic electron microscopy (cryo-EM) Nuclear magnetic resonance (NMR), and X-ray crystallography.

In some embodiments, the IL-2 variant may be stabilized in a dimeric form by forming IL-2 variant-dimerization domain conjugates. Such conjugates can be formed by fusing IL-2 variant monomers to a dimerization domain, wherein each of the two dimerization domain monomers is linked to one IL-2 variant monomer directly or indirectly via a linker. The dimerization domain may be a homodimer or heterodimer capable of stabilizing the IL-2 variant at least partially (e.g., partially, predominantly, entirely) in a dimeric form. Such dimerization domain may include a dimeric immunoglobulin Fc region, a GST protein, and the like.

In some embodiments, the dimerization domain may include a dimeric immunoglobulin Fc region (e.g., IgG-Fc, IgG4-Fc). The term "immunoglobulin Fc region," as used herein, refers to a protein that contains the heavy-chain constant region 2 (CH2) and the heavy-chain constant region 3 (CH3) of an immunoglobulin, excluding the heavy-chain and light-chain variable regions, the heavy-chain constant region 1 (CH1) and the light-chain constant region 1 (CL1) of the immunoglobulin. The immunoglobulin Fc region may further include a hinge region in the heavy-chain constant region. Also, the immunoglobulin Fc region in the present invention may be an extended Fc region that contains a portion or the whole of the heavy-chain constant region 1 (CH1) and/or the light-chain constant region 1 (CL1), except for the heavy-chain and light-chain variable regions, as long as it has a physiological function substantially equal to or better than the native form. Further, it may be a fragment having a deletion in a relatively long portion of the amino acid sequence of CH2 and/or CH3.

In other words, the immunoglobulin Fc region in the present invention may comprise (1) a CH1 domain, a CH2 domain, a CH3 domain, and a CH4 domain, (2) a CH1 domain and a CH2 domain, (3) a CH1 domain and a CH3 domain, (4) a CH2 domain and a CH3 domain, (5) a combination of one or more domains and an immunoglobulin hinge region (or a portion of the hinge region), and (6) a dimer of each domain of the heavy-chain constant regions and the light-chain constant region.

In the present invention, the immunoglobulin Fc fragment is meant to include not only a native amino acid sequence, but also a mutant sequence thereof. As used herein, the term "amino acid sequence mutant" refers to a sequence that is different from the native amino acid sequence due to a deletion, insertion, non-conservative or conservative substitution or combinations thereof of one or more amino acid residues.

The immunoglobulin Fc region may originate from humans or animals such as cattle, goats, pigs, mice, rabbits, hamsters, rats, or guinea pigs. In some embodiments, each of the immunoglobulin Fc monomers may be independently derived from IgG, IgA, IgD, IgE and IgM, combinations thereof, or hybrids thereof. In some embodiments, each of the immunoglobulin Fc monomers may be independently derived from IgG or IgM, which is among the most abundant proteins in the human blood. In some embodiments, a dimeric Fc region may be formed of two Fc region monomers from the same or different origins. In addition, each Fc region monomer can be a hybrid Fc region. As used herein, the term "hybrid" means that sequences encoding two or more immunoglobulin Fc fragments of different origins are present in a single-chain immunoglobulin Fc fragment. In the present invention, various types of hybrids are possible. In other words, domain hybrids may be composed of one to four domains selected from the group consisting of CH1, CH2, CH3, and CH4 of IgG Fc, IgM Fc, IgA Fc, IgE Fc, and IgD Fc, and may include a hinge region.

In addition, IgG can be divided into IgG1, IgG2, IgG3, and IgG4 subclasses, and combinations or hybrids thereof may be used in the present invention. In some embodiments, the IgG2 and IgG4 subclasses are used in the present invention.

In some embodiments, the isolated IL-2 variant comprises a polypeptide sequence having at least 80% (e.g., 80%, 85%, 90%, 95%, 99%) identity to SEQ ID NOs: 11-12 or a polypeptide sequence of SEQ ID NO: 11 or 12.

The linker can be a peptide linker and a non-peptide linker. Examples of the peptide linker may include [Ser(Gly)n]m or [Ser(Gly)n]mSer, where n may be an integer between 1 and 20, and m may be an integer between 1 and 10. For example, the peptide linker can be SerGly, SerGlySer, SerGlyGly, SerGlyGlySer, SerGlyGlyGly, SerGlyGlyGly-Ser, SerGlyGlyGlyGly, SerGlyGlyGly GlySer, SerGlyGlyGlyGlyGly, SerGlyGlyGlyGlyGlySer, SerGlyGlyGlyGly GlyGly, and SerGly GlySerGlyGlyGlyGlySer.

As used herein, the term "non-peptide linker" refers to a biocompatible polymer composed of two or more repeating units linked to each other, in which the repeating units are linked to each other by any non-peptide covalent bond. This non-peptidyl linker may have two ends or three ends. Examples of the non-peptidyl linker may include, without limitation, polyethylene glycol, polypropylene glycol, a copolymer of ethylene glycol with propylene glycol, polyoxyethylated polyol, polyvinyl alcohol, polysaccharide, dextran, polyvinyl ethyl ether, biodegradable polymers such as polylactic acid (PLA) and polylactic-glycolic acid (PLGA), lipid polymers, chitins, hyaluronic acid, and combinations thereof.

Alternatively, the IL-2 variant may be stabilized in a dimeric form via an in vitro modification, for example, through crosslinking with a crosslinking agent, e.g., crosslinker. Crosslinkers are reagents having reactive ends to specific functional groups (e.g., primary amines or sulfhydryls) on proteins or other molecules. Crosslinkers are capable of joining two or more molecules by a covalent bond. Crosslinkers include but are not limited to amine-toamine crosslinkers (e.g., disuccinimidyl suberate (DSS)), amine-to-sulfhydryl crosslinkers (e.g., N-γ-maleimidobutyryl-oxysuccinimide ester (GMBS)), carboxyl-to-amine crosslinkers (e.g., dicyclo-hexylcarbodiimide (DCC)), sulfhydryl-to-carbohydrate crosslinkers (e.g., N-s-maleimidopropionic acid hydrazide (BMPH)), sulfhydryl-to-sulfhydryl crosslinkers (e.g., 1,4-bismaleimidobutane (BMB)), photoreactive crosslinkers (e.g., N-5-azido-2-nitrobenzoyloxysuccinimide (ANB-NOS)), chemoselective ligation crosslinkers (e.g., NHS-PEG4-Azide).

d. IL-2/IL-2Rα Complex

This disclosure also encompasses an IL-2/IL-2Rα complex (or IL-2/IL-2Rα heterodimer). In some embodiments, the IL-2/IL-2Rα complex has abolished or reduced binding to endogenous IL-2Rα expressed on cell surface, but have intact affinity to IL-2Rβ/γ dimeric receptor. In some embodiments, the IL-2/IL-2Rα complex can be formed and stabilized by paired cysteine substitutions (see, e.g., TABLE 2 below) that can be introduced on both IL-2 and IL-2Rα sides at their binding interface to allow the formation of a stable disulfide-bonded IL-2/IL-2Rα complex. The paired cysteine substitutions can be generated based on the structure-based rational design approach (e.g., based on X-ray crystal structure of the IL-2/IL-2Rα complex; see PDB: 2B5I). For example, pairs of residues on the IL-2 and IL-2Rα binding interface can be selected based on one or more of the following criteria: (i) after a pair of residues are substituted with cysteine, the sides chains of the cysteines are in a distance sufficient to form a disulfide bond. In some embodiments, the distance can be between about 1.8 Å and about 2.2 Å; (ii) the cysteine substitutions should not significantly disrupt the folding of IL-2 and/or IL-2Rα; and (iii) the cysteine substitutions should not significantly reduce the solubility and/or stability of IL-2 and/or IL-2Rα.

TABLE 2

Example paired cysteine substitutions on IL-2 and/or IL-2Rα

| IL-2 | IL-2Ra |
|---|---|
| F42C | L42C |
| E61C | K38C |
| K64C | S39C |
| P65C | L42C |
| P34C | D4C |
| E61C | S39C |
| E68C | L42C |

e. Compositions and Kits

The present invention also provides a composition, e.g., a pharmaceutical composition, containing one or a combination of the IL-2 variants of the present invention, formulated together with a pharmaceutically acceptable carrier. Such compositions may include one or a combination of (e.g., two or more different) IL-2 variants of the invention. For example, a pharmaceutical composition of the invention can comprise a combination of the IL-2 variants having different genetic modifications.

Pharmaceutical compositions or therapeutic formulations of the IL-2 variant can be prepared by mixing the IL-2 variant having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed and include buffers such as phosphate, citrate, and other organic acids; antioxidants including ascorbic acid and methionine; preservatives (e.g., octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONIC, or polyethylene glycol (PEG).

The formulation may also contain more than one active ingredients as necessary for the particular indication being treated, preferably those with complementary activities that do not adversely affect each other. For instance, the formulation may further comprise another IL-2 variant, cytotoxic agent, or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethyl cellulose or gelatin-microcapsule and poly-(methylmethacrylate) microcapsule, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the IL-2 variant, which matrices are in the form of shaped articles, e.g., films, or microcapsule. Examples of sustained-releasable matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-d(−)-3-hydroxybutyric acid (PHB). While polymers such as ethylene-vinyl acetate and lactic acid-glycolic acid enable release of molecules for over 100 days, certain hydrogels release proteins for shorter time periods. When encapsulated IL-2 variant molecules remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thiol-disulfide interchange, stabilization may be achieved by modifying sulfhydryl residues, lyophilizing from acidic solutions, controlling moisture content, using appropriate additives, and developing specific polymer matrix compositions.

The formulations to be used for in vivo administration must be sterile, which can be readily accomplished by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

In some embodiments, the pharmaceutical compositions may include at least one other therapeutic agent. For example, the pharmaceutical composition may further include an anti-cancer or anti-tumor agent, including chemotherapeutic agents and immunotherapeutic agents.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, methyldopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189, and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g., calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, xeloda, gemcitabine, KRAS mutation covalent inhibitors, and goserelin; and pharmaceutically acceptable salts, acids or derivatives of any of the above. Additional examples include irinotecan, oxaliplatinum, and other standard colon cancer regimens.

An "immunotherapeutic agent" is a biological agent useful in the treatment of cancer. Examples of immunotherapeutic agents include atezolizumab, avelumab, blinatumomab, daratumumab, cemiplimab, durvalumab, elotuzumab, laherparepvec, ipilimumab, nivolumab, obinutuzumab, ofatumumab, pembrolizumab, cetuximab, talimogene, and the like.

Alternatively, the immunotherapeutic agent can be an immune checkpoint modulator, such as an antibody specific for CTLA-4, PD-1, PD-L1, PD-L2, killer immunoglobulin receptor (KIR), LAG3, B7-H3, B7-H4, TIM3, A2aR, CD40L, CD27, OX40, 4-IBB, TCR, BTLA, ICOS, CD28, CD80, CD86, ICOS-L, B7-H4, HVEM, 4-1BBL, OX40L, CD70, CD40, GALS or the like.

The active compounds can be prepared with carriers that will protect the compound against rapid release, such as a controlled release formulation, including implants, transdermal patches, and microencapsulated delivery systems. Biodegradable, biocompatible polymers can be used, such as ethylene-vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

The pharmaceutical compositions may be prepared, packaged, or sold in the form of a sterile injectable aqueous or oily suspension or solution. This suspension or solution may be formulated according to the known art and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

This disclosure further provides kits containing one or more components, such as the above-described IL-2 variant, the polynucleotide encoding the IL-2 variant, the vector including the polynucleotide, the host cell, and a combination thereof. The kits of the invention can be provided at any suitable temperature. For example, for storage of kits containing protein components or complexes thereof in a liquid, it is preferred that they are provided and maintained below 0° C., preferably at or below −20° C., or otherwise in a frozen state.

A kit may contain the components in an amount sufficient for single use. In some applications, one or more components may be provided in pre-measured single-use amounts in individual, typically disposable, tubes, or equivalent containers. The amount of a component supplied in the kit can be any appropriate amount and may depend on the target market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the components in any of a variety of configurations (e.g., in a vial, microtiter plate well, microarray, and the like). The kits may further include instructions recorded in a tangible form for the use of the components.

In some embodiments, the instant disclosure provides a pharmaceutical kit of parts comprising an IL-2 variant and an anti-cancer or anti-tumor agent, such as an immune checkpoint modulator (e.g., an anti-CTLA-4 and/or anti-PD-1 antibody). The kit may also further comprise instructions for use in the treatment of a hyperproliferative disease (such as cancer as described herein). In some embodiments, the IL-2 variant and/or the anti-cancer or anti-tumor agent may be co-packaged in a unit dosage form. In some embodiments, IDO inhibitors may also be combined with the above treatments to further enhance the anti-tumor activity of IL-2 variant treatment.

B. METHODS OF USING IL-2 VARIANTS a. Methods for Modulating $T_{reg}$ Cell Activity

In one aspect, this disclosure provides a method of reducing $T_{reg}$ cell activity. The method comprises administering a therapeutically effective amount of the isolated IL-2 variant or the pharmaceutical composition, as described above, to a subject in need thereof. In some embodiments, the subject may have or be suspected of a cancer or tumor. In some embodiments, the subject exhibits reduced adverse events as compared to a subject treated with human wild-type IL-2.

By "regulatory T cell" or "$T_{reg}$ cell" is meant a specialized type of $CD4^+$ T cell that can suppress the responses of other T cells. $T_{reg}$ cells are characterized by expression of the a-subunit of the IL-2 receptor (CD25) and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. $T_{reg}$ cells require IL-2 for their function and development and induction of their suppressive characteristics.

The terms "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

The term "effective amount," "effective dose," or "effective dosage" is defined as an amount sufficient to achieve or at least partially achieve a desired effect.

In many embodiments, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). The subject may be a human or a non-human. In more exemplary aspects, the mammal is a human. As used herein, the expression "a subject in need thereof" or "a patient in need thereof" means a human or non-human mammal that exhibits one or more symptoms or indications of cancer or tumor, and/or who has been diagnosed with tumor or cancer, including a solid tumor and who needs treatment for the same. The expression includes subjects with primary, established, or recurrent tumor lesions. In specific embodiments, the expression includes human subjects that have and/or need treatment for a solid tumor. The expression also includes subjects with primary or metastatic tumors (advanced malignancies). In certain embodiments, the expression includes patients with a solid tumor that is resistant to or refractory to or is inadequately controlled by prior therapy (e.g., surgery or treatment with an anti-cancer agent such as carboplatin or docetaxel). In certain embodiments, the expression includes patients with a tumor lesion that has been treated with one or more lines of prior therapy (e.g., surgically removed), but which has subsequently recurred. In some embodiments, the expression includes subjects with a tumor or cancer who are not candidates for curative surgery or curative radiation, or for whom conventional anti-cancer therapy is inadvisable, for example, due to toxic side effects. In other embodiments, the expression includes subjects with a tumor lesion for which surgical removal is planned. In other embodiments, the expression includes subjects for whom the risk of recurrence is high due to a prior history of recurrence after surgery.

As used to describe the present invention, "cancer," "tumor," and "malignancy" all relate equivalently to hyperplasia of a tissue or organ. If the tissue is a part of the lymphatic or immune system, malignant cells may include non-solid tumors of circulating cells. Malignancies of other tissues or organs may produce solid tumors. The methods of the present invention may be used in the treatment of lymphatic cells, circulating immune cells, and solid tumors.

Cancers that can be treated include tumors that are not vascularized or are not substantially vascularized, as well as vascularized tumors. Cancers may comprise non-solid tumors (such as hematologic tumors, e.g., leukemias and lymphomas) or may comprise solid tumors. The types of cancers to be treated with the compositions of the present invention include, but are not limited to, carcinoma, blastoma and sarcoma, and certain leukemias or malignant lymphoid tumors, benign and malignant tumors and malignancies, e.g., sarcomas, carcinomas, and melanomas. Also included are adult tumors/cancers and pediatric tumors/cancers.

Hematologic cancers are cancers of the blood or bone marrow. Examples of hematologic (or hematogenous) cancers include leukemias, including acute leukemias (such as acute lymphocytic leukemia, acute myelocytic leukemia, acute myelogenous leukemia, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high-grade forms), myeloma Multiple, Waldenstrom's macroglobulinemia, heavy chain disease, myelodysplastic syndrome, hairy cell leukemia, and myelodysplasia.

Solid tumors are abnormal masses of tissue that usually do not contain cysts or liquid areas. Solid tumors can be benign or malignant. The different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma and other sarcomas, synovium, mesothelioma, Ewing tumor, leiomyosarcoma, rhabdomyosarcoma, colon carcinoma, lymphoid malignancy, pancreatic cancer, breast cancer, lung cancer, ovarian cancer, prostate cancer, hepatocellular carcinoma, squamous cell carcinoma, basal cell carcinoma, adenocarcinoma, carcinoma of the sweat gland, medullary thyroid carcinoma, papillary thyroid carcinoma, sebaceous gland carcinoma of pheochromocytomas, carcinoma papillary, papillary adenocarcinomas, medullary carcinoma, bronchogenic carcinoma, renal cell carcinoma, hepatoma, bile duct carcinoma, choriocarcinoma, Wilms tumor, cervical cancer, testicular tumor, seminoma, bladder carcinoma, melanoma, and CNS tumors (such as glioma, e.g., brainstem glioma and mixed gliomas), glioblastoma (e.g., astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma, and brain metastasis).

In some embodiments, the cancer or tumor is selected from the group consisting of oral cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer, and skin cancer.

b. Methods of Treating Cancer

In yet another aspect, this disclosure additionally provides a method of treating or inhibiting a tumor. The method comprises administering a therapeutically effective amount of the isolated IL-2 variant or the pharmaceutical composition, as described above, a subject in need thereof.

As used herein, the terms "treating," "treat," or the like, refer to alleviating or reducing the severity of at least one symptom or indication, eliminating the causation of symptoms either on a temporary or permanent basis, delaying or inhibiting tumor growth, reducing tumor cell load or tumor burden, promoting tumor regression, causing tumor shrinkage, necrosis and/or disappearance, preventing tumor recurrence, preventing or inhibiting metastasis, inhibiting metastatic tumor growth, eliminating the need for surgery, and/or increasing duration of survival of the subject.

Administration and Dosage Regimens

In some embodiments, the additional therapeutic agent is administered to the subject before, after, or concurrently with the second therapeutic agent. The IL-2 variant can be administered as a single dose or more commonly can be administered on multiple occasions. Intervals between single dosages can be, for example, weekly, monthly, every three months or yearly. Intervals can also be irregular as indicated by measuring blood levels of IL-2 variant to the target antigen in the patient.

The isolated IL-2 variant or the pharmaceutical composition can be administered via one or more routes of administration using one or more of a variety of methods known in the art. As will be appreciated by the skilled artisan, the route and/or mode of administration will vary depending upon the desired results. Preferred routes of administration for IL-2 variants of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion. Alternatively, an IL-2 variant of the invention can be administered via a non-parenteral route, such as a topical, epidermal or mucosal route of administration, for example, intranasally, orally, vaginally, rectally, sublingually or topically.

In some embodiments, the isolated IL-2 variant or the pharmaceutical composition can be administered intratumorally, intravenously, subcutaneously, intraosseously, orally, transdermally, in sustained release, in controlled release, in delayed release, as a suppository, or sublingually.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active ingredient for the treatment of sensitivity in individuals.

For administration of the IL-2 variant, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration daily, twice per week, once per week, once every two weeks, once every three weeks, once every four weeks, once a month, once every 3 months or once every three to 6 months. For example, dosage regimens for an IL-2 variant of the invention include 0.2-10 mg/kg body weight via intravenous administration.

Alternatively, the IL-2 variant can be administered as a sustained release formulation, in which case less frequent administration is required. Dosage and frequency vary depending on the half-life of the IL-2 variant in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular active ingredient being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an IL-2 variant of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth or metastasis by at least about 20%, more preferably by at least about 40%, even more preferably by at least about 60%, and still more preferably by at least about 80% relative to untreated subjects. The ability of an agent to inhibit tumor growth can be evaluated in an animal model system predictive of efficacy in human tumors. Alternatively, this property of a composition can be evaluated by examining the ability of the agent to inhibit, such inhibition in vitro by assays known to the skilled practitioner. A therapeutically effective amount of a therapeutic composition can decrease tumor size, metastasis, or otherwise ameliorate symptoms in a subject. One of ordinary skill in the art would be able to determine such amounts based on such factors as the subject's size, the severity of the subject's symptoms, and the particular composition or route of administration selected.

A "prophylactically effective amount" or a "prophylactically effective dosage" of a drug is an amount of the drug that, when administered alone or in combination with another therapeutic agent to a subject at risk of developing a disease (e.g., cancer) or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

Pharmaceutical compositions can be administered with medical devices known in the art. For example, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, and 4,596,556. Examples of well-known implants and modules useful in the present invention include those described in U.S. Pat. Nos. 4,487,603, 4,486,194, 4,447,233, 4,447,224, 4,439,196, and 4,475,196. These patents are incorporated herein by reference. Many other such implants, delivery systems, and modules are known to those skilled in the art.

Combination Therapies

Pharmaceutical compositions of the present invention can be administered in combination therapy, i.e., co-administered with other therapeutic agents. For example, the combination therapy can include an IL-2 variant of the present invention combined with at least one other therapeutic agent, such as an anti-cancer or anti-tumor agent, including chemotherapeutic agents and immunotherapeutic agents, as provided above.

As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

For example, the IL-2 variants may also be combined with standard cancer treatments, such as chemotherapeutic regimes. Examples of the chemotherapeutic regimes are provided above. In these instances, it may be possible to reduce the dose of chemotherapeutic reagent administered (Mokyr, M. et al. (1998) Cancer Research 58: 5301-5304). An example of such a combination is an IL-2 variant in combination with dacarbazine for the treatment of melanoma. Other combination therapies that may result in synergy with IL-2 variants through cell death are radiation, surgery, and hormone deprivation. In some embodiments, angiogenesis inhibitors may also be combined with IL-2 variants.

In some embodiments, IL-2 variants may be combined with the antibodies used to activate host immune responsiveness. Such antibodies may include molecules on the surface of dendritic cells that activate DC function and antigen presentation. For example, anti-CD40 antibodies are able to substitute effectively for T cell helper activity (Ridge, J. et al. (1998) Nature 393: 474-478) and can be used in conjunction with IL-2 variants. Similarly, activating antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), PD-1 (U.S. Pat. No. 8,008,449), PD-1L (U.S. Pat. Nos. 7,943,743 and 8,168,179) and ICOS (Hutloff, A. et al. (1999) Nature 397: 262-266) may also provide for increased levels of T cell activation.

In some embodiments, IL-2 variants may be combined with adoptive cell therapies (ACT) to promote the expansion, activation, tumor infiltration and persistence of transferred cells. Such cells may include but not limited to CAR-T or CAR-NK cells, expanded tumor-infiltration lymphocytes, tumor-specific T cells, and the like.

In some embodiments, an IL-2 variant can be used in conjunction with anti-neoplastic antibodies, such as RITUXAN (rituximab), HERCEPTIN (trastuzumab), BEXXAR (tositumomab), ZEVALIN (ibritumomab), CAMPATH (alemtuzumab), LYMPHOCIDE (pertuzumab), AVASTIN (bevacizumab), and TARCEVA (erlotinib), and the like.

In some embodiments, the present disclosure provides a method for treating a tumor, comprising co-administering an IL-2 variant and an immune checkpoint modulator (e.g., an anti-CTLA-4 antibody) to a subject. For example, the IL-2 variant can be administered at a subtherapeutic dose, and the immune checkpoint modulator can be administered at a subtherapeutic dose, or both are administered at a subtherapeutic dose. In some embodiments, the present invention provides a method for altering an adverse event associated with treatment of a hyperproliferative disease with an immunostimulatory agent, comprising administering an IL-2 variant and a subtherapeutic dose of an immune checkpoint modulator to a subject.

C. ADDITIONAL DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The terms "polypeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, pegylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, a "wild-type" form of IL-2 is a form of IL-2 that is otherwise the same as the mutant IL-2 polypeptide except that the wild-type form has a wild-type amino acid at each amino acid position of the mutant IL-2 polypeptide. For example, if the IL-2 mutant is the full-length IL-2 (i.e., IL-2 not fused or conjugated to any other molecule), the wild-type form of this mutant is full-length native IL-2. If the IL-2 mutant is a fusion between IL-2 and another polypeptide encoded downstream of IL-2 (e.g., an antibody chain), the wild-type form of this IL-2 mutant is IL-2 with a wild-type amino acid sequence fused to the same downstream polypeptide. Furthermore, if the IL-2 mutant is a truncated form of IL-2 (the mutated or modified sequence within the non-truncated portion of IL-2), then the wild-type form of this IL-2 mutant is a similarly truncated IL-2 that has a wild-type sequence.

The term "recombinant," as used herein, refers to proteins or fragments thereof of the present disclosure created, expressed, isolated, or obtained by technologies or methods known in the art as recombinant DNA technology which include, e.g., DNA splicing and transgenic expression. The term refers to fusion proteins expressed in a non-human mammal (including transgenic non-human mammals, e.g., transgenic mice), or a cell (e.g., CHO cells) expression system or isolated from a recombinant combinatorial human antibody library.

The term "operably linked" refers to a functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein, the term "promoter" or "regulatory sequence" refers to a nucleic acid sequence which is required for expression of a gene product operably linked to the promoter/regulatory sequence. In some instances, this sequence may be the core promoter sequence, and in other instances, this sequence may also include an enhancer sequence and other regulatory elements that are required for expression of the gene product. The promoter or regulatory sequence may, for example, be one that expresses the gene product in a tissue-specific manner. An "inducible" promoter is a nucleotide sequence that, when operably linked with a polynucleotide that encodes or specifies a gene product, causes the gene product to be produced in a cell substantially only when an inducer that corresponds to the promoter is present in the cell.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product(s)." If the polynucleotide is derived from genomic DNA, expression may include splicing of the mRNA in a eukaryotic cell.

By "isolated" nucleic acid molecule or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference.

The term "disease" as used herein is intended to be generally synonymous and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the term "modulate" is meant to refer to any change in biological state, i.e., increasing, decreasing, and the like.

The terms "increased," "increase" or "enhance" or "activate" are all used herein to generally mean an increase by a statically significant amount; for the avoidance of any doubt, the terms "increased," "increase" or "enhance" or "activate" means an increase of at least 10% as compared to a reference level, for example, an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

"Sample," "test sample," and "patient sample" may be used interchangeably herein. The sample can be a sample of serum, urine plasma, amniotic fluid, cerebrospinal fluid, cells, or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

As used herein, the term "composition" or "pharmaceutical composition" refers to a mixture of at least one component useful within the invention with other components, such as carriers, stabilizers, diluents, dispersing agents, suspending agents, thickening agents, and/or excipients. The pharmaceutical composition facilitates administration of one or more components of the invention to an organism.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

The term "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of one or more components of the invention, and are physiologically acceptable to the subject. Supplementary active compounds may also be incorporated into the compositions.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. EXAMPLES

The following examples are put forth so as to provide those of ordinary skill in the art with a complete disclosure and description of how to make and use the methods and compositions of the present disclosure and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1

This example describes the materials and methods used in EXAMPLES 2-7 below.

Mutant IL-2 Protein Expression and Purification

Expi293FTM cells (THERMO FISHER SCIENTIFIC) were transiently transfected with plasmids encoding different IL-2 mutants fused to a Myc-Myc-6×His (mmh) tag. Supernatants (sups) from transfected cells were analyzed by SDS-PAGE under a non-reducing condition (FIG. 1). The expressed proteins were detected by blotting with an anti-Myc antibody (INVITROGEN).

To purify expressed proteins from Expi293F sups, the sups were buffer exchanged to phosphate-buffered saline (PBS) through dialysis before being loaded to a HisTalon Superflow column (CLONTECH) at 4° C. at 0.5 ml/min. The column was washed sequentially with washer buffer I (PBS+500 mM NaCl) and washer buffer II (PBS+500 mM NaCl, 5 mM Imidazole). The protein was then eluted with elution buffer (PBS+500 mM NaCl, 200 mM Imidazole), followed by buffer exchange to PBS+5% Glycerol. To separate IL-2 (E68C) dimer and monomer, the eluted protein was furthered purified through Size Exclusion Chromatography (SEC) using two tandemly connected Superdex75 10/300 GL columns (GE Healthcare) for small scale purification or a Superdex200 26/60 prep grade column (GE Healthcare) for a larger scale preparation. The purity of the proteins was confirmed by SDS-PAGE, analytical SEC, and intact mass analysis.

Hydrogen Deuterium Exchange Mass Spectrometry

Figure 2A:
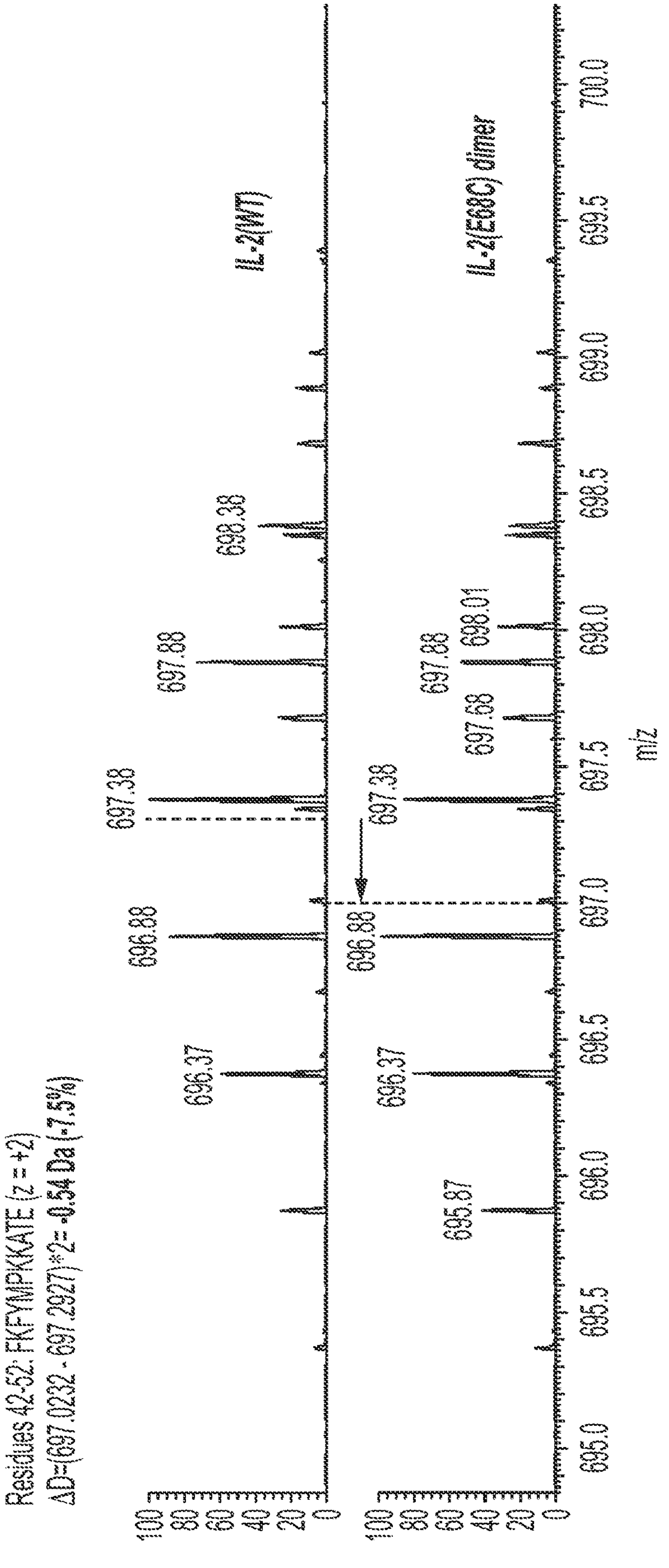
FIGS. 2A and 2B show characterization of the hIL-2 (E68C) dimeric interface. Hydrogen deuterium exchange mass spectrometry (HDX-MS) was used to map the dimeric interface of hIL-2 (E68C).
Figure 2A:
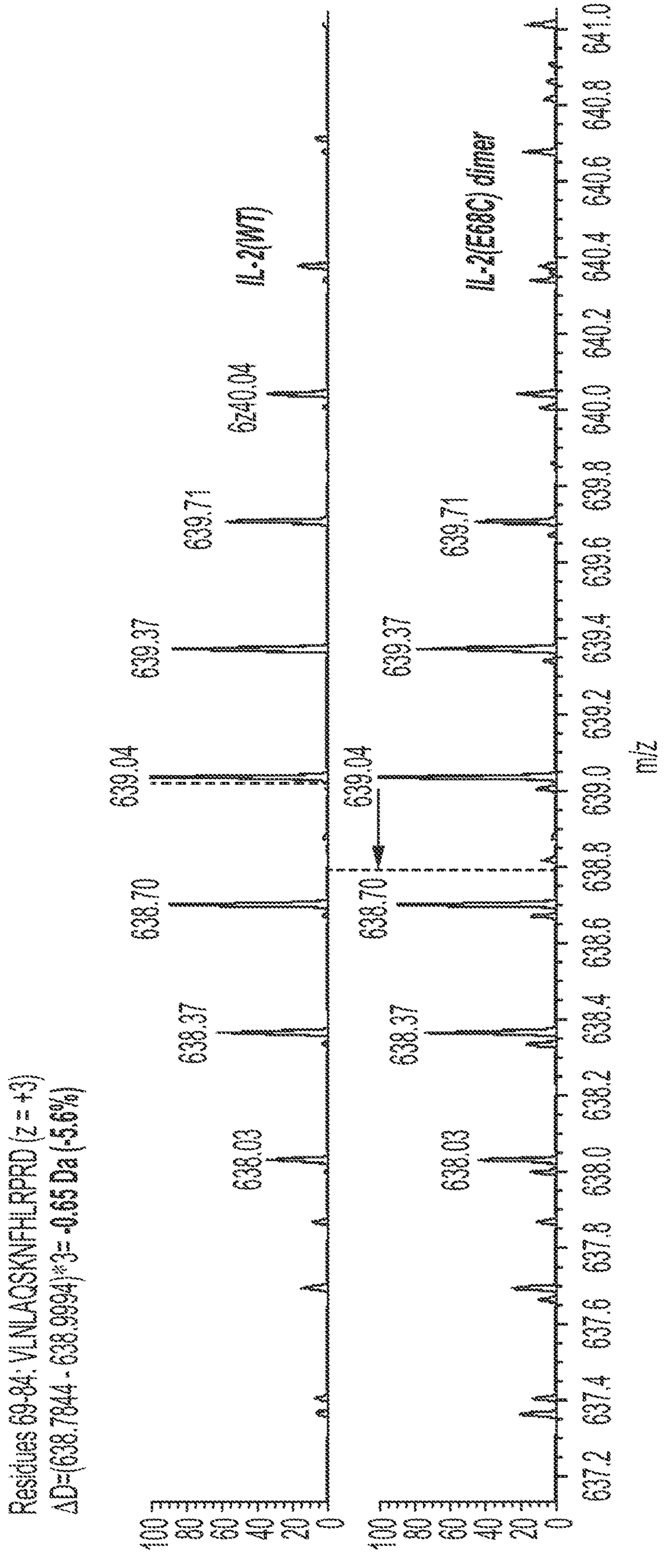

Hydrogen-deuterium exchange (HDX) mass spectrometry (MS) was used to map the IL-2 (E68C) dimeric interface (FIG. 2A). The HDX-MS experiments were performed on an integrated HDX/MS platform consisting of a Leaptec HDX PAL system for the deuterium labeling and quenching, a Waters Acquity M-Class (Auxiliary solvent manager) for the sample digestion and loading, a Waters Acquity M-Class (pBinary solvent manager) for the analytical gradient, and Thermo Q Exactive HF mass spectrometer for peptide mass measurement.

The labeling solution was prepared as PBS buffer in D20 at pD 7.0 (10 mM phosphate buffer, 140 mM NaCl, and 3 mM KCl, equivalent to pH 7.4 at 25° C.). For deuterium labeling, hIL2-mmH (Regeneron in house protein REGN7183) or hIL2(E68C)-mmH (REGENERON in house protein REGN7184) was incubated at 20° C. with D20 labeling solution for various time-points in duplicates (e.g., Undeuterated control=0 second; deuterium-labeled for 5 minutes and 10 minutes). The deuteration reaction was quenched by adding pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10% to 32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of the undeuterated IL-2 sample were searched against a database including IL-2 and its reversed sequence using Byonic search engine (PROTEIN METRICS). The search parameters were set to default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D). Any peptide which exhibited a differential percent D-uptake value above 5% was defined as significantly protected.

STAT5-Luciferase Reporter Assay

NK-92 cell stably expressing STAT3-luciferase reporter (NK92-STAT3-Luc) were plated at 30,000/well in 50 µl culture media without IL-2 and incubated overnight. The next day, 50p of 1:5 serially diluted IL-2 variant was added to each well, with the final concentration of each IL-2 variant starting at 100 nM. After 5.5 hour incubation at 37° C., the plates were equilibrated at room temperature for 15 minutes. 100 µl of One-Glo substrate (PROMEGA) was added to each well, and luminescence was measured on an Envision plate reader (PERKINELMER).

Intracellular Staining of pSTAT5 on Human PBMCs

Cryopreserved human PBMCs were thawed and rested overnight in media without IL-2. The next day, cells were treated with serial dilutions of different IL-2 variants, then fixed with BD CYTOFIX fixation buffer at 37° C. for 12 min. Cells were then permeabilized with pre-chilled BD Phosflow™ Perm Buffer III for 20 min on ice. Cells were then washed twice with FACS buffer (PBS+2% FBS), followed by incubation with a staining cocktail containing ALEXA FLUOR 647-conjugated anti-STAT5 pY694 (BD BIOSCIENCES) at room temperature for 45 min in the dark. To identify different lymphocyte populations in PBMCs, the following panel of antibodies were also included in the staining cocktail: BUV496-anti-CD8, BUV395-anti-CD4, BV421-anti-NKp46, BV711-anti-CD56, BV786-anti-CD3, ALEXA FLUOR 488-anti-FoxP3, PE-anti-CD25 (BD Biosciences). Cells were washed twice with FACS buffer before data acquisition on a BD LSRFORTESSA X-20 flow cytometer. The raw data were analyzed with FlowJo v10.

Mice Treatment and FACS Analyses of Splenocytes

C57BL/6J mice were treated daily with intraperitoneal injection of different IL-2 variants for seven consecutive days. One day after the last injection, spleens were collected and mashed through a 70-µm CORNING cell strainer to generate single-cell suspensions. Splenocytes were then treated with ACK lysing buffer (LONZA) to lyse red blood cells (RBCs). After RBC lysis, cells were counted and stained with antibody cocktails diluted in BD Horizon Brilliant Buffer. The stained samples were analyzed on a BD LSRFORTESSA X-20 flow cytometer. The raw data were processed with FlowJo v10.

Example 2

To reduce IL-2 binding to endogenous IL-2Rα, a panel of single cysteine mutations (e.g., WT, P34C, F42C, E61C, K64C, P65C, and E68C) were introduced to human IL-2 at its binding interface to IL-2Rα. As showed in FIG. 1, while most mutations result in noticeably decreased expression/secretion of IL-2 in culture media supernatant, the E68C mutation leads to formation of a disulfide-bridged IL-2 dimer, appearing as a band with a visually doubled molecular weight of WT IL-2 on non-reducing SDS-PAGE.

Example 3

Figure 2B:
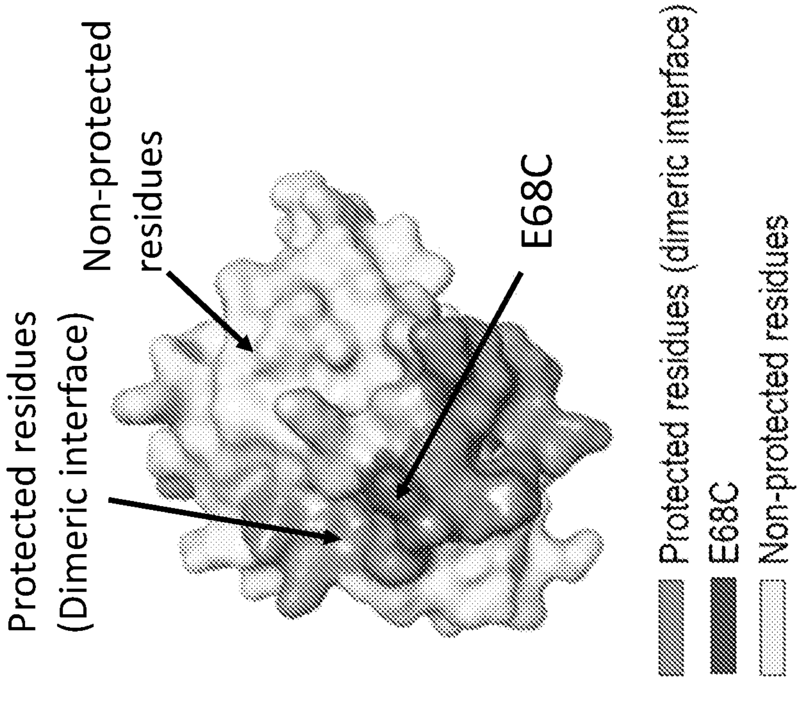

As shown in FIGS. 2A and 2B, hydrogen-deuterium exchange mass spectrometry (HDX-MS) was used to map the dimeric interface of hIL-2 (E68C). Mass spectra of indicated peptides from D2O-treated IL-2(WT) or IL-2 (E68C) protein samples (FIG. 2A). Dashed lines indicate the centroid masses of each peptide in indicated samples. Arrows indicate shifts in the centroid mass of the same peptide from different samples. Differences in the percentage of deuterium uptake (% D) for each peptide were shown. Compared to corresponding peptides from IL-2(WT) monomer, two peptides from hIL-2(E68C) dimer were significantly protected from deuterium uptake. These two peptides correspond to residues 42-52 (FKFYMPKKATE) and 69-84 (VLNLAQSKNFHLRPRD) and appear to surround the mutated E68C residue. FIG. 2B shows a surface structure model of human IL-2 (PDB: 1M47) with the positions of protected residues and mutated E68C residue indicated.

Example 4

Figure 3A:
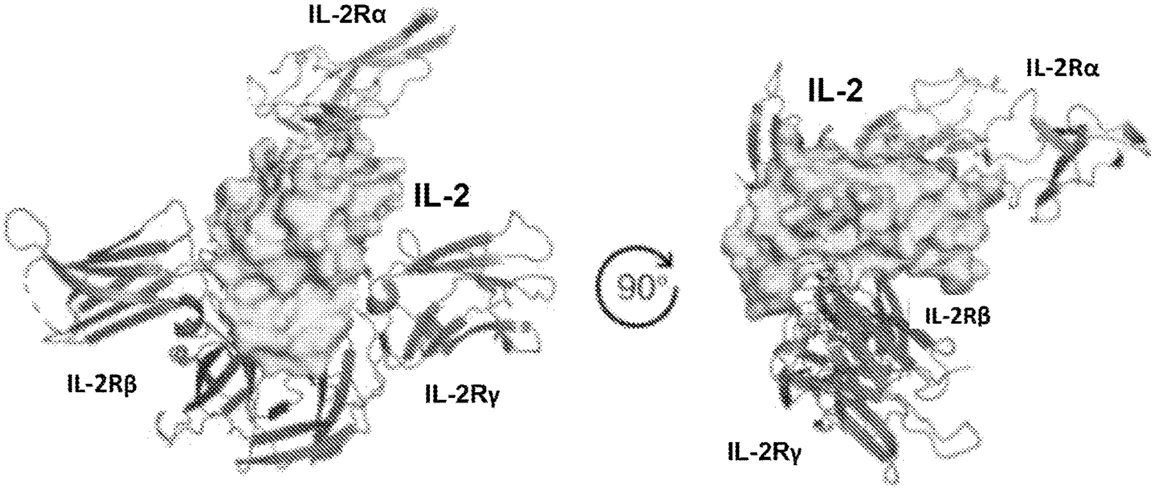
FIGS. 3A and 3B show the structural models of IL-2 receptors in complex with IL-2 WT or variants.
Figure 3B:
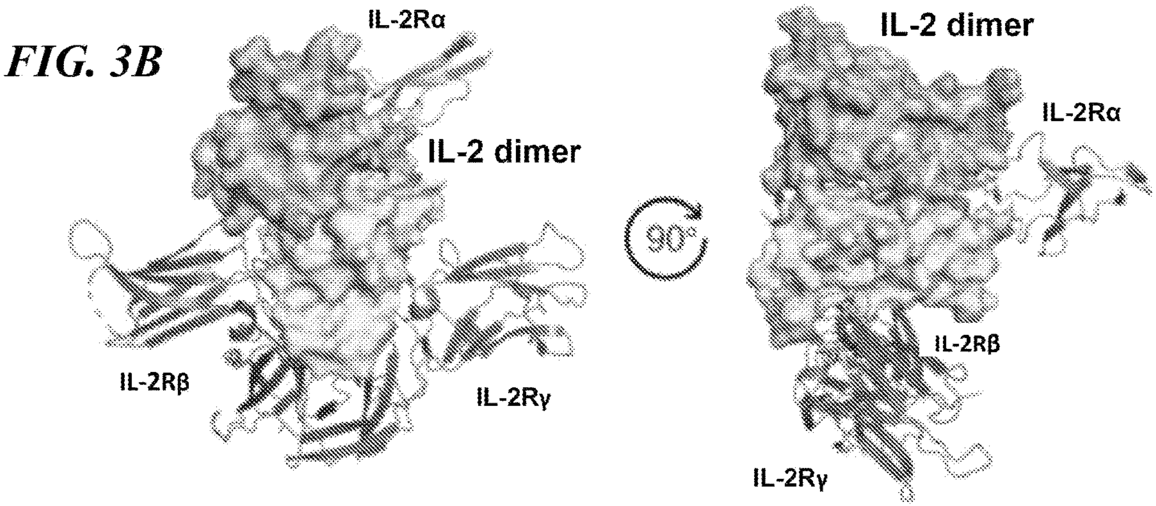

FIGS. 3A and 3B show the structural models of IL-2 receptors in complex with IL-2 WT or variants. FIG. 3A shows a structural representation of IL-2 receptors (IL-2α, IL-2β, and IL-2γ) in complex with IL-2 (WT) (PDB: 2B5I). IL-2(E68C). FIG. 3B shows a structural representation of IL-2 receptors (IL-2α, IL-2β, and IL-2γ) in complex with modeled IL-2(E68C) dimer based on the dimeric interface shown in FIG. 2B. When the modeled dimer was fitted into the structure of IL-2R complex, it became clear that the dimeric interface overlaps with the IL-2/IL-2Rα binding interface, resulting in precluded binding of the dimer to IL-2Rα. In contrast, as there is no overlap between the dimeric interface and IL-2/IL-2Rβ/IL-2Rγ binding interfaces, the IL-2 dimer should interact with IL-2Rβ and IL-2Rγ in a manner identical to IL-2(WT).

Example 5

Figure 4A:
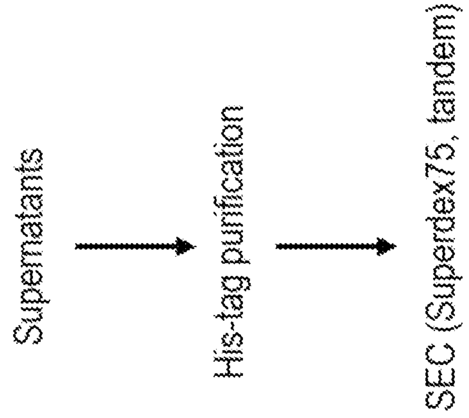
FIGS. 4A, 4B, and 4C show purification and characterization of IL-2(E68C).
Figure 4B:
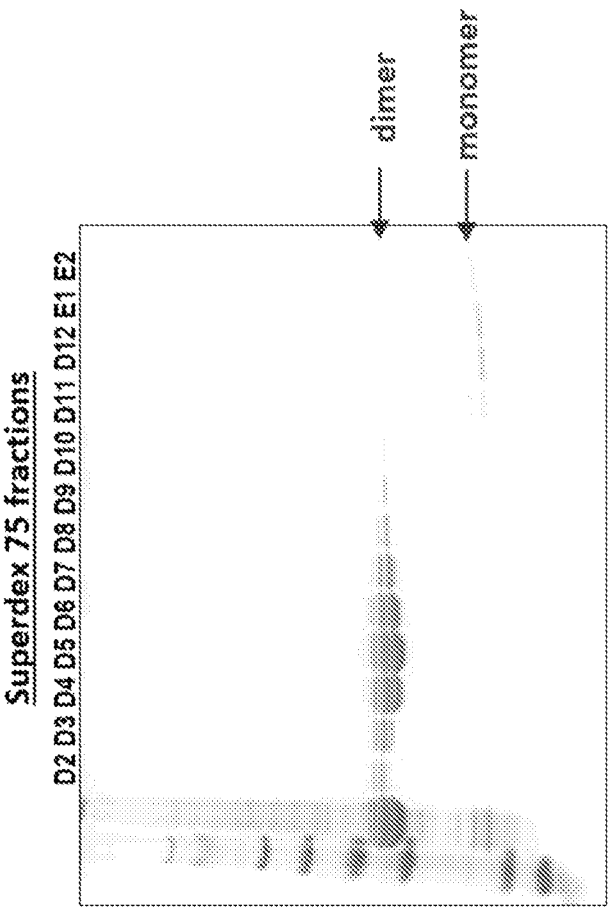
Figure 4C:
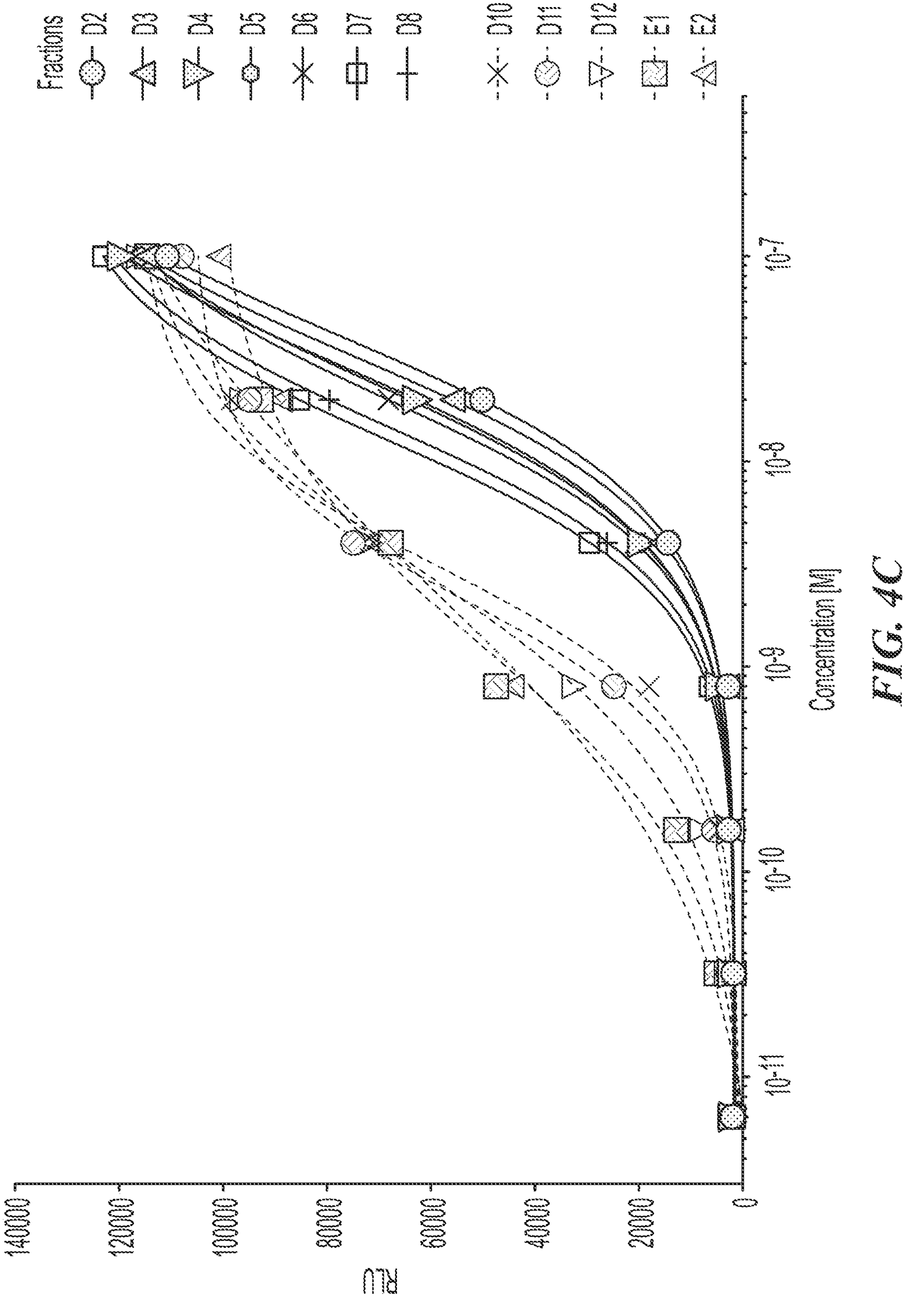

FIGS. 4A, 4B, and 4C show purification and characterization of IL-2(E68C). FIG. 4A shows a purification scheme of IL-2(E68C)-mmh protein. Aliquots of each fraction from the Superdex 75 column were analyzed by SDS-PAGE followed by staining with Coomassie blue (FIG. 4B) and tested for their activity on NK92-STAT3-Luc cells (FIG. 4C). IL-2(E68C)-mmh dimer and monomer was purified from media supernatant of transfected Expi293F cells through two steps of chromatography: affinity with cobalt resin and size exclusion using two Superdex 75 columns connected in tandem. The activity in each Superdex75 fraction was assayed on NK92-STAT3-Luc cells (IL-2Rα+β+γ+). The dose-response curves for all fractions fall into two distinct groups, with dimer fractions showing reduced activity compared to monomer fractions.

Example 6

Figure 5A:
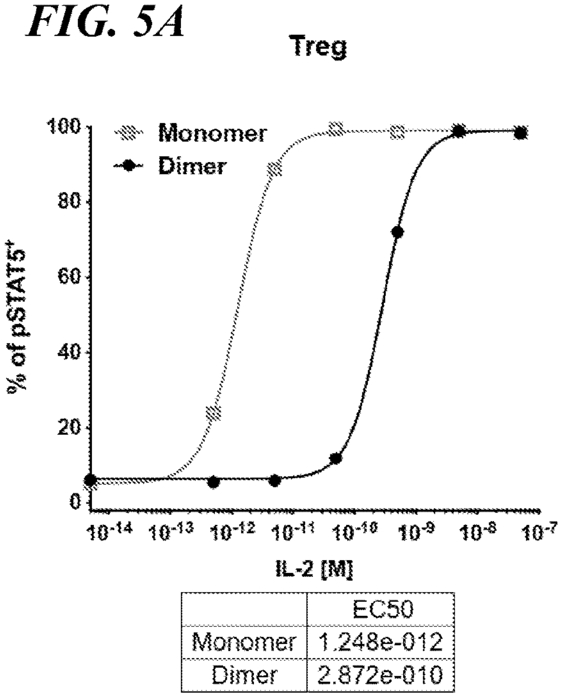
FIGS. 5A, 5B, and 5C show the effects of dimerization of IL-2 on the activity of Tregs, CD8+ T cells, and NK cells. Human PBMCs were stimulated with increasing concentrations of IL-2(E68C) monomer or dimer. Percentage of cells underwent STAT5 phosphorylation within gated Tregs (FIG. 5A), CD8+ T cells (FIG. 5B), and NK cells (FIG. 5C) was evaluated by flow cytometry. EC50 values corresponding to each dose-response curve were indicated thereunder.
Figure 5B:
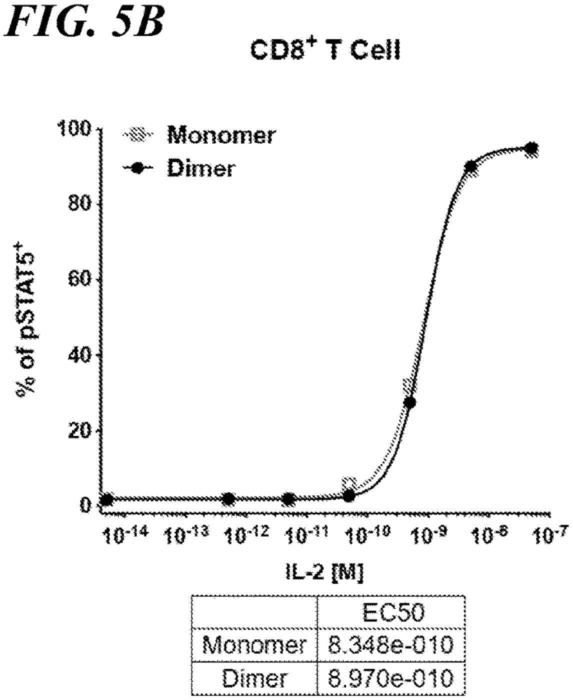
Figure 5C:
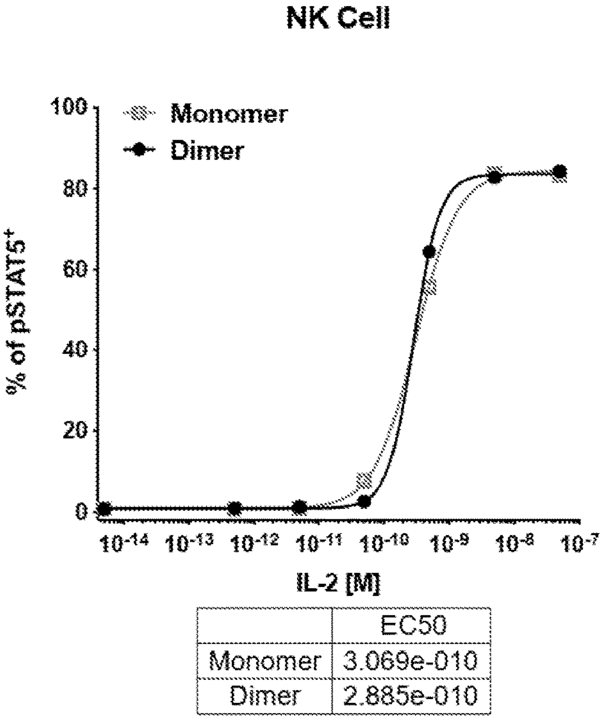

To study the effects of dimerization of IL-2 on activity of Tregs, CD8+ cells, and NK cells (FIGS. 5A, 5B, and 5C), human PBMCs were stimulated with increasing concentrations of IL-2(E68C) monomer or dimer. Percentage of cells underwent STAT5 phosphorylation within gated Tregs (FIG. 5A), CD8+ T cells (FIG. 5B), and NK cells (FIG. 5C) was evaluated by flow cytometry. EC50 values corresponding to each dose-response curve were indicated thereunder. Compared to the monomer, IL-2(E68C) dimer remains equally active on CD8+T and NK cells, which lack detectable IL-2Rα expression. However, its activity on IL-2Rα+ Tregs became at least two orders of magnitude lower than that of monomer. Therefore, IL-2(E68C) dimer loses the preferential activity on Tregs over other effector cell populations in vitro.

Example 7

Figure 6A:
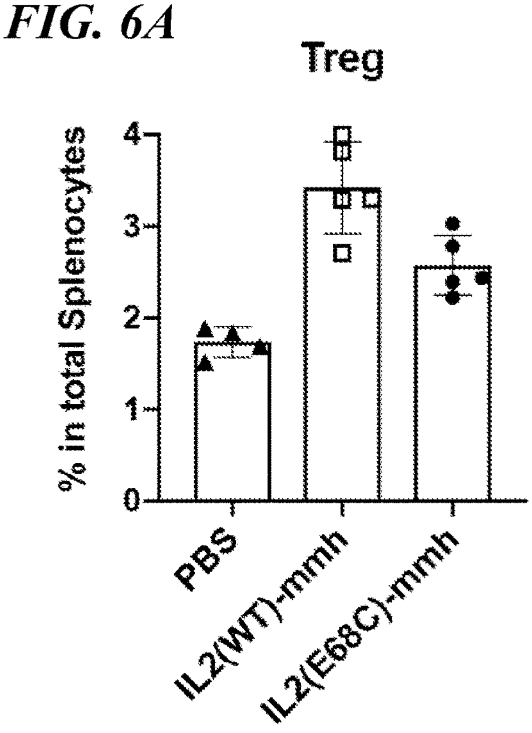
FIGS. 6A, 6B, and 6C show the effects of dimerization of IL-2 on expansion of Tregs, CD8+ T cells, and NK cells. C57BL/6J mice received daily intraperitoneal injection of PBS, 30 μg IL2(WT)-mmh or 30 μg IL2(E68C)-mmh for seven consecutive days. One day after the last injection, spleens were harvested for flow cytometric analysis. Percentage of Treg (FIG. 6A), CD8+ T cell (FIG. 6B), and NK cell (FIG. 6C) and in total splenocytes of treated mice in each group were quantified.
Figure 6B:
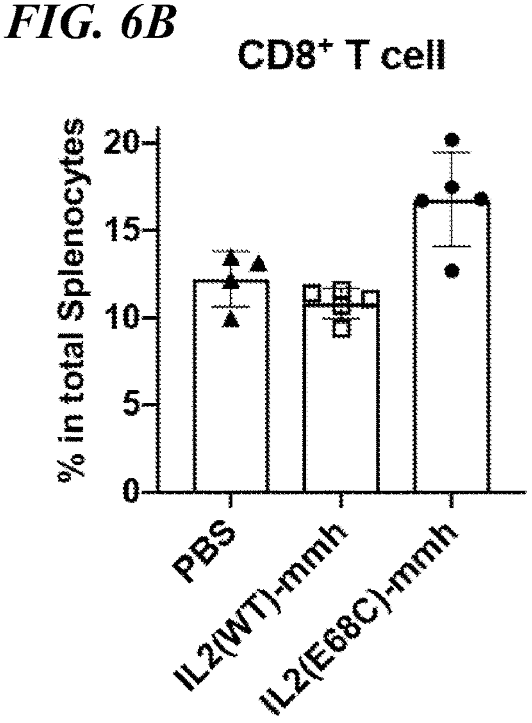
Figure 6C:
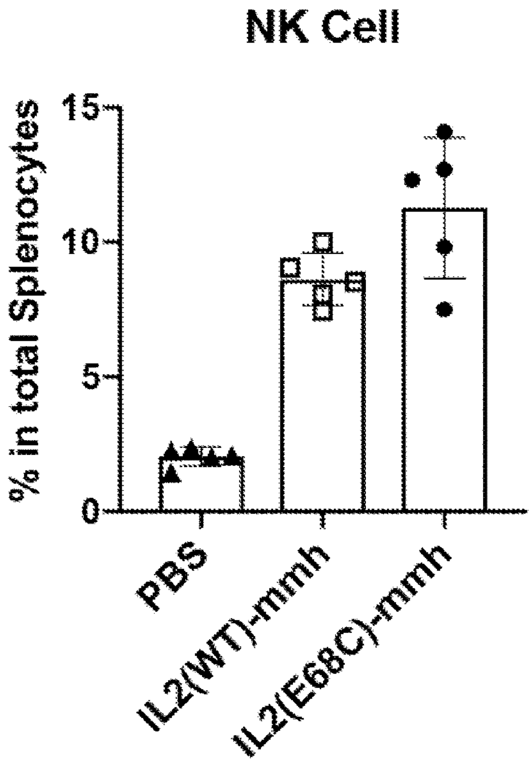

To study the effects of dimerization of IL-2 on expansion of Tregs, CD8+ cells, and NK cells. C57BL/6J mice received daily intraperitoneal injection of PBS, 30 μg IL2 (WT)-mmh or 30 μg IL2(E68C)-mmh for seven consecutive days (FIGS. 6A, 6B, and 6C). One day after the last injection, spleens were harvested for flow cytometric analysis. Percentage of Treg (FIG. 6A), CD8+ T cell (FIG. 6B), and NK cell (FIG. 6C) and in total splenocytes of treated mice in each group were quantified. While IL-2(WT) preferentially expands Tregs in vivo, such Treg-selectivity was reduced in IL-2(E68C) dimer. In contrast, IL-2(E68C) dimer induces specific expansion of NK and CD8+ T cells with much attenuated effect on the Treg compartment. Thus, IL-2(E68C) dimer can remodel the lymphocyte compartment in vivo by selectively fueling the effector cell populations.

Example 8

This example describes an IL-2 reporter assay and the use of this assay to assess the ability of IL2-mmh (REGN7183; SEQ ID NO: 2), IL2(E68C)-mmh (REGN7184; SEQ ID NO: 3), IL2-Fc (REGN8189; SEQ ID NO: 11), and IL2 (3m)-Fc (REGN8190; SEQ ID NO: 12) fusion constructs in inducing IL-2Ra dependent and independent IL2 receptor signaling. IL2(3m)-Fc (REGN8190) contains three mutations in IL2, namely, F42A, Y45A, L72G ((numbering based on UniProt ID P60568 excluding the signal peptide) (Klein et al., OncoImmunology, 6:3 (2017)).

Cell Line Engineering

Engineering of YT/reporter cells: The human T/NK cell leukemia YT cell line was electroporated with a Signal Transducer and Activator of Transcription 5 (STAT5)-luciferase reporter construct and maintained in Iscoves+20% FBS+P/S/G+200 μg/mL hygromycin. A single cell clone, having high responsiveness to IL-2, was identified and renamed YT/Stat5-Luc c1.4. IL2Ra (CD25) expression was assessed by flow cytometry (2,500 antibody binding capacity (ABC)), and knocked out in this clone using CRISPR-Cas9 technology. The resulting cell line, YT/STAT5-Luc/IL2Ra KO, was validated by flow cytometry. Human IL2Ra was then stably reintroduced into the YT/STAT5-Luc/IL2Ra KO cell line (amino acids Ml-1272 of accession number NP_000408.1) and the resulting cell line, YT/STAT5-Luc/hIL2Ra, was validated by flow cytometry (250,000 ABC). Cells were maintained in Iscoves+20% FBS+P/S/G+200 μg/mL hygromycin+15 μg/mL blasticidin.

IL2 Reporter Assay

In this experiment, engineered YT reporter cells are stimulated via either recombinant IL2-Fc in-line fusion, an IL2-myc.myc.his tagged (IL2-mmh), an IL2(E68C)-mmh or an IL2(F62A,Y65A,L92G)-Fc (IL2(3m)-Fc). Functional IL2 receptors are formed by the differential assembly of IL2R subunits (IL2Ra, IL2Rb and IL2Rg), with assembly of the IL2Rb/IL2Rg subunits comprising a low affinity receptor and receptors containing all three subunits (IL2Ra/IL2Rb/IL2Rg) forming a high affinity receptor. Binding of cytokine by IL2R leads to activation of STAT5, which drives luciferase production in the engineered cell lines. To assess the relative potency of each construct in the presence of the low affinity (IL2Rb/g) IL2 receptor or the high affinity (IL2Ra/b/g) IL2 receptor, reporter cells were engineered to lack or overexpress IL2Ra.

Assay Set Up

Opti-MEM media supplemented with 1% bovine serum albumin (BSA) was used as assay medium to prepare cell suspensions and antibody dilutions. A day prior to screening, engineered reporter YT/Stat5-Luc cells over-expressing or devoid of IL2Ra were diluted at $3\times10^5$ cells/mL. On the day of the assay, cells were spun down, resuspended in assay medium, plated at $2.5\times10^4$ reporter cells/well in 96 well white flat bottom plates and incubated with IL2-mmh (REGN7183), IL2(E68C)-mmh (REGN7184), IL2-Fc (REGN8189) or IL2(3m)-Fc (REGN8190) serially diluted (1:4) over an 11-point titration range (150 nM to 143 fM), with the $12^{th}$ point containing no recombinant protein. Plates were incubated for 4 hours at 37° C./5% $CO_2$, and then 100 µL ONE-Glo™ (Promega) reagent was added to the wells to lyse the cells and detect luciferase activity. The emitted light was measured in RLU on a multilabel plate reader Envision (PerkinElmer). $EC_{50}$ values of the antibodies were determined using GraphPad Prism™ software from a four-parameter logistic equation over a 12-point dose-response curve.

Results Summary

The ability of IL2-mmh, IL2(E68C)-mmh, IL2-Fc and IL2(3m)-Fc fusion constructs to induce IL-2Ra dependent and independent IL2 receptor signaling was assessed using a STAT5-reporter assay.

Figure 7A:
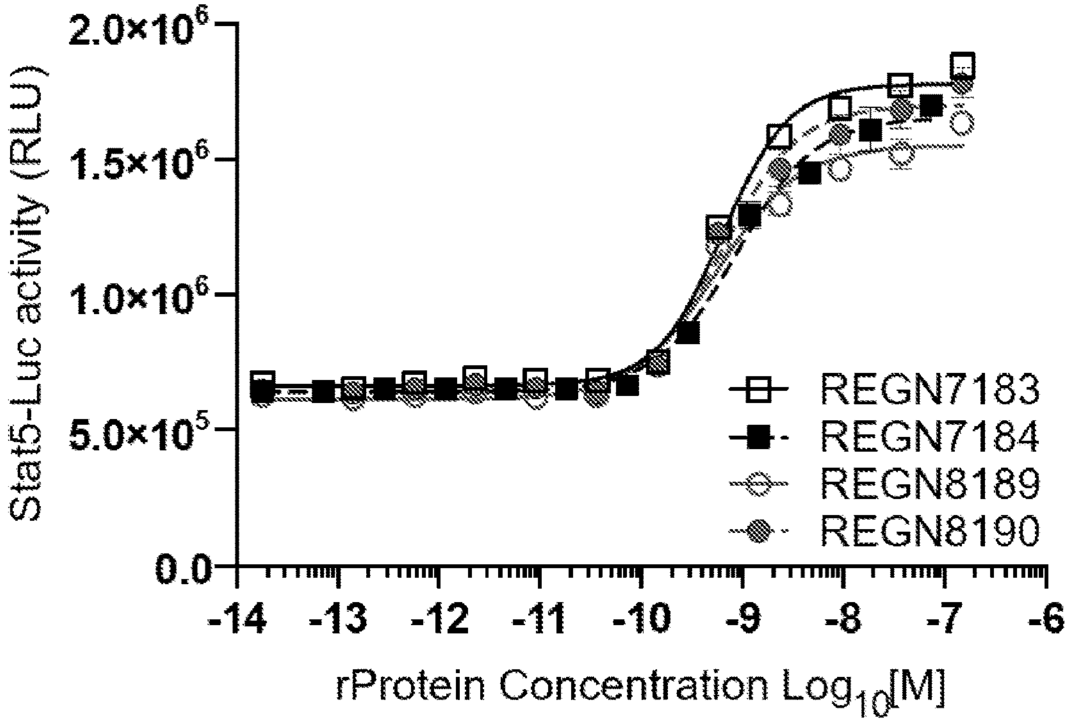
FIGS. 7A and 7B show an IL2 reporter assay. YT/STAT5-Luc/hIL2Ra KO (FIG. 7A) or YT/STAT5-Luc/hIL2Ra (FIG. 7B) were incubated with a titration of IL2-mmh (black open square with black solid line; REGN7183), IL2(E68C)-mmh (black solid square with black dashed line; REGN7184), IL2-Fc (gray open circle with gray solid line; REGN8189) or IL2(E68C)-mmh (gray solid circle with gray dashed line; REGN8190). Four hours later, STAT5 activity was assessed by luminescent readout.
Figure 7B:
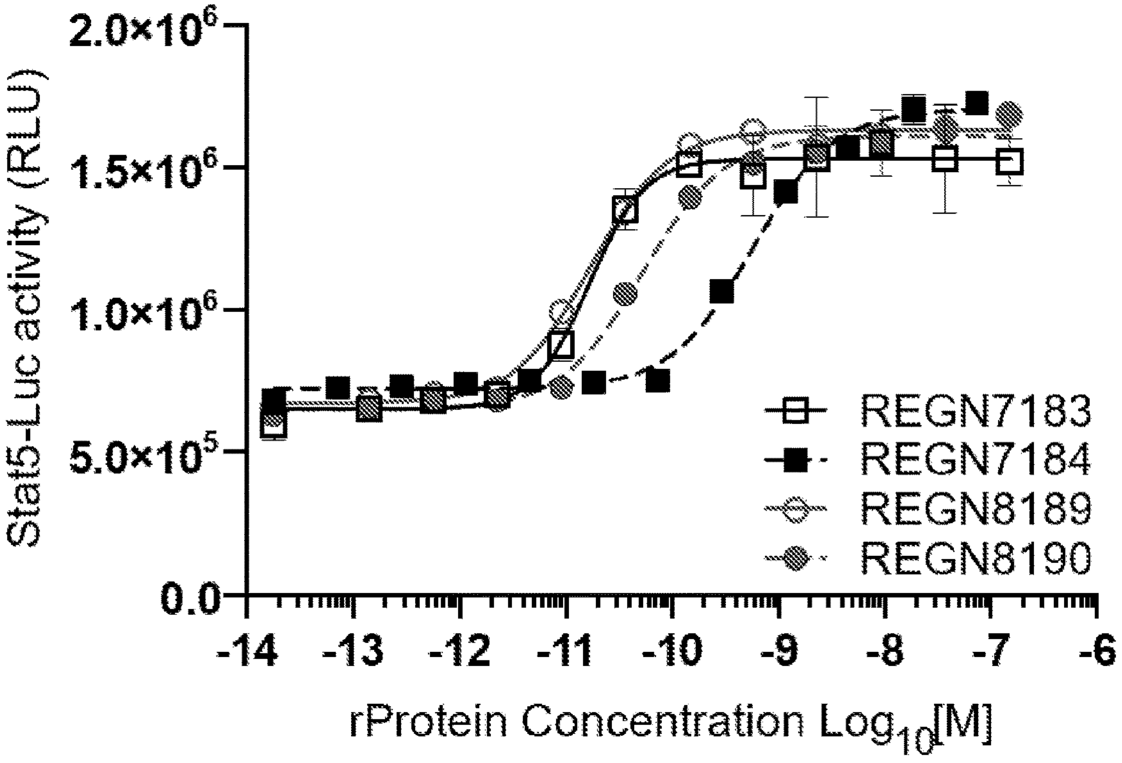

YT/STAT5-Luc/hIL2Ra or YT/STAT5-Luc/IL2Ra KO reporter cells were incubated with either IL2-mmh (REGN7183), IL2(E68C)-mmh (REGN7184), IL2-Fc (REGN8189) or IL2(3m)-Fc (REGN8190) and STAT5 reporter activity was assessed. Activation curves are shown in FIGS. 7A and 7B and $EC_{50}$ values are summarized in TABLE 3.

While all IL-2 constructs had similar potency on the YT/STAT5-Luc/IL2Ra KO cell line, the IL2(E68C)-mmh (REGN7184) construct exhibited 34-fold less potency as compared to IL2-mmh (REGN7183) on YT/STAT5-Luc/hIL2Ra cells, and the IL2(3m)-Fc (REGN8190) construct exhibited 3-fold less potency as compared to IL2-Fc (REGN8189) on YT/STAT5-Luc/hIL2Ra cells.

TABLE 3

IL2 reporter assay - Summary of $EC_{50}$ values:

| | REGN7183 | REGN7184 | REGN8189 | REGN8190 |
|---|---|---|---|---|
| YT/Stat5-Luc/IL2Ra KO | 6.222E−10 | 8.465E−10 | 5.419E−10 | 6.284E−10 |
| YT/Stat5-Luc/hIL2Ra | 1.647E−11 | 5.630E−10 | 1.693E−11 | 5.170E−11 |

Tabulated IL2 reporter assay summarizing $EC_{50}$ for IL2-mmh, IL2(E68C)-mmh, IL2-Fc, and IL2(3m)-Fc constructs.

The present disclosure is not to be limited in scope by the specific embodiments described herein. Indeed, various modifications of the present disclosure in addition to those described herein will become apparent to those skilled in the art from the foregoing description and the accompanying figures. Such modifications are intended to fall within the scope of the appended claims.

SEQUENCE LISTING

```
Sequence total quantity: 12
SEQ ID NO: 1            moltype = AA  length = 153
FEATURE                 Location/Qualifiers
source                  1..153
                        mol_type = protein
                        organism = Homo sapiens
SEQUENCE: 1
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 2            moltype = AA  length = 161
FEATURE                 Location/Qualifiers
REGION                  1..161
                        note = with a C-terminal myc-myc-hexahistidine (mmh) tag
source                  1..161
                        mol_type = protein
                        organism = synthetic construct
SEQUENCE: 2
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTEQKLISE EDLGGEQKLI SEEDLHHHHH H                      161

SEQ ID NO: 3            moltype = AA  length = 161
FEATURE                 Location/Qualifiers
REGION                  1..161
                        note = hIL2(E68C)-mmh
source                  1..161
                        mol_type = protein
                        organism = synthetic construct
SEQUENCE: 3
APTSSSTKKT QLQLEHLLLD LQMILNGINN YKNPKLTRML TFKFYMPKKA TELKHLQCLE  60
EELKPLECVL NLAQSKNFHL RPRDLISNIN VIVLELKGSE TTFMCEYADE TATIVEFLNR  120
WITFCQSIIS TLTEQKLISE EDLGGEQKLI SEEDLHHHHH H                      161

SEQ ID NO: 4            moltype = AA  length = 133
FEATURE                 Location/Qualifiers
```

-continued

```
REGION                  1..133
                        note = hIL-2(E68C)
source                  1..133
                        mol_type = protein
                        organism = synthetic construct
SEQUENCE: 4
APTSSSTKKT QLQLEHLLLD LQMILNGINN YKNPKLTRML TFKFYMPKKA TELKHLQCLE  60
EELKPLECVL NLAQSKNFHL RPRDLISNIN VIVLELKGSE TTFMCEYADE TATIVEFLNR  120
WITFCQSIIS TLT                                                     133

SEQ ID NO: 5            moltype = AA  length = 133
FEATURE                 Location/Qualifiers
REGION                  1..133
                        note = hIL-2(P34C)
source                  1..133
                        mol_type = protein
                        organism = synthetic construct
SEQUENCE: 5
APTSSSTKKT QLQLEHLLLD LQMILNGINN YKNCKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 6            moltype = AA  length = 133
FEATURE                 Location/Qualifiers
REGION                  1..133
                        note = hIL-2(F42C)
source                  1..133
                        mol_type = protein
                        organism = synthetic construct
SEQUENCE: 6
APTSSSTKKT QLQLEHLLLD LQMILNGINN YKNPKLTRML TCKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 7            moltype = AA  length = 133
FEATURE                 Location/Qualifiers
REGION                  1..133
                        note = hIL-2(E61C)
source                  1..133
                        mol_type = protein
                        organism = synthetic construct
SEQUENCE: 7
APTSSSTKKT QLQLEHLLLD LQMILNGINN YKNPKLTRML TFKFYMPKKA TELKHLQCLE  60
CELKPLEEVL NLAQSKNFHL RPRDLISNIN VIVLELKGSE TTFMCEYADE TATIVEFLNR  120
WITFCQSIIS TLT                                                     133

SEQ ID NO: 8            moltype = AA  length = 133
FEATURE                 Location/Qualifiers
REGION                  1..133
                        note = hIL-2(K64C)
source                  1..133
                        mol_type = protein
                        organism = synthetic construct
SEQUENCE: 8
APTSSSTKKT QLQLEHLLLD LQMILNGINN YKNPKLTRML TFKFYMPKKA TELKHLQCLE  60
EELCPLEEVL NLAQSKNFHL RPRDLISNIN VIVLELKGSE TTFMCEYADE TATIVEFLNR  120
WITFCQSIIS TLT                                                     133

SEQ ID NO: 9            moltype = AA  length = 133
FEATURE                 Location/Qualifiers
REGION                  1..133
                        note = hIL-2(P65C)
source                  1..133
                        mol_type = protein
                        organism = synthetic construct
SEQUENCE: 9
APTSSSTKKT QLQLEHLLLD LQMILNGINN YKNPKLTRML TFKFYMPKKA TELKHLQCLE  60
EELKCLEEVL NLAQSKNFHL RPRDLISNIN VIVLELKGSE TTFMCEYADE TATIVEFLNR  120
WITFCQSIIS TLT                                                     133

SEQ ID NO: 10           moltype = DNA  length = 402
FEATURE                 Location/Qualifiers
misc_feature            1..402
                        note = cDNA sequence of hIL-2(E68C)
source                  1..402
                        mol_type = other DNA
                        organism = synthetic construct
SEQUENCE: 10
gcacctactt caagttctac aaagaaaaca cagctacaac tggagcattt actgctggat  60
```

-continued

```
ttacagatga ttttgaatgg aattaataat tacaagaatc ccaaactcac caggatgctc  120
acatttaagt tttacatgcc caagaaggcc acagaactga aacatcttca gtgtctagaa  180
gaagaactca aacctctgga gtgtgtgcta aatttagctc aaagcaaaaa ctttcactta  240
agacccaggg acttaatcag caatatcaac gtaatagttc tggaactaaa gggatctgaa  300
acaacattca tgtgtgaata tgctgatgag acagcaacca ttgtagaatt tctgaacaga  360
tggattacct tttgtcaaag catcatctca acactgactt ga                     402

SEQ ID NO: 11          moltype = AA  length = 366
FEATURE                Location/Qualifiers
REGION                 1..366
                       note = Synthetic
source                 1..366
                       mol_type = protein
                       organism = synthetic construct
SEQUENCE: 11
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSES KYGPPCPPCP APPVAGPSVF LFPPKPKDTL MISRTPEVTC  180
VVVDVSQEDP EVQFNWYVDG VEVHNAKTKP REEQFNSTYR VVSVLTVLHQ DWLNGKEYKC  240
KVSNKGLPSS IEKTISKAKG QPREPQVYTL PPSQEEMTKN QVSLTCLVKG FYPSDIAVEW  300
ESNGQPENNY KTTPPVLDSD GSFFLYSRLT VDKSRWQEGN VFSCSVMHEA LHNHYTQKSL  360
SLSLGK                                                             366

SEQ ID NO: 12          moltype = AA  length = 366
FEATURE                Location/Qualifiers
REGION                 1..366
                       note = Synthetic
source                 1..366
                       mol_type = protein
                       organism = synthetic construct
SEQUENCE: 12
APTSSSTKKT QLQLEHLLLD LQMILNGINN YKNPKLTRML TAKFAMPKKA TELKHLQCLE  60
EELKPLEEVL NGAQSKNFHL RPRDLISNIN VIVLELKGSE TTFMCEYADE TATIVEFLNR  120
WITFCQSIIS TLTGGGGSES KYGPPCPPCP APPVAGPSVF LFPPKPKDTL MISRTPEVTC  180
VVVDVSQEDP EVQFNWYVDG VEVHNAKTKP REEQFNSTYR VVSVLTVLHQ DWLNGKEYKC  240
KVSNKGLPSS IEKTISKAKG QPREPQVYTL PPSQEEMTKN QVSLTCLVKG FYPSDIAVEW  300
ESNGQPENNY KTTPPVLDSD GSFFLYSRLT VDKSRWQEGN VFSCSVMHEA LHNHYTQKSL  360
SLSLGK                                                             366
```

We claim:

1. An isolated polynucleotide molecule comprising a polynucleotide sequence that encodes an isolated interleukin-2 (IL-2) variant comprising the polypeptide sequence as set forth in SEQ ID NO: 4.

2. The polynucleotide molecule of claim 1, comprising a polynucleotide sequence of SEQ ID NO: 10.

3. A vector comprising the polynucleotide molecule of claim 2.

4. A host cell comprising the vector of claim 3.

5. A method for producing a polypeptide, comprising culturing the host cell of claim 4 under conditions in which the polynucleotide molecule is expressed.

* * * * *